US008716461B2

(12) United States Patent
Delwart et al.

(10) Patent No.: US 8,716,461 B2
(45) Date of Patent: May 6, 2014

(54) HUMAN PARVOVIRUS

(75) Inventors: Eric L. Delwart, San Francisco, CA (US); Morris S. Jones, Walnut Creek, CA (US)

(73) Assignee: Blood Systems, Inc., Scottsdale, AZ (US)

( * ) Notice: Subject to any disclaimer, the term of this patent is extended or adjusted under 35 U.S.C. 154(b) by 1443 days.

(21) Appl. No.: 11/569,554

(22) PCT Filed: May 24, 2005

(86) PCT No.: PCT/US2005/018314
§ 371 (c)(1), (2), (4) Date: Nov. 22, 2006

(87) PCT Pub. No.: WO2006/065273
PCT Pub. Date: Jun. 22, 2006

(65) Prior Publication Data
US 2009/0162831 A1 Jun. 25, 2009

Related U.S. Application Data

(60) Provisional application No. 60/574,430, filed on May 24, 2004.

(51) Int. Cl.
*C12N 15/35* (2006.01)
*C12N 15/63* (2006.01)
*C12N 5/10* (2006.01)

(52) U.S. Cl.
USPC ..................... 536/23.72; 435/320.1; 435/325

(58) Field of Classification Search
None
See application file for complete search history.

(56) References Cited

U.S. PATENT DOCUMENTS

| | | | | |
|---|---|---|---|---|
| 5,935,794 | A * | 8/1999 | Kambara et al. | 435/6 |
| 7,655,785 | B1 * | 2/2010 | Bentwich | 536/24.1 |
| 2004/0110930 | A1 * | 6/2004 | Reinl et al. | 530/387.1 |

FOREIGN PATENT DOCUMENTS

WO   WO 02/22826   *   3/2002   ............. C12N 15/52

OTHER PUBLICATIONS

Genbank locus AJ429915 (Jan. 30, 2003).*
Allander et al., "A virus discovery method incorporating DNase treatment and its application to the identification of two bovine parvovirus species," *Proc Natl Acad Sci USA* 98:11609-11614 (2001).
Breitbart et al., "Genomic analysis of uncultured marine viral communities," *Proc. Natl. Acad. Sci. USA* 99:14250-14255 (2002).
Breitbart et al., "Metagenomic analyses of an uncultured viral community from human feces," *J. Bacteriol.* 185:6220-6223 (2003).
Durigon et al., "Multiple primer pairs for polymerase chain reaction (PCR) amplification of human parvovirus B19 DNA," *J Virol Methods* 44: 155-65 (1993).
Fukada et al., "Four putative subtypes of human parvovirus B19 based on amino acid polymorphism in the C-terminal region of non-structural protein," *J. Med. Virol.* 62:60-69 (2000).
Lukashov and Goudsmit, "Evolutionary relationships among parvoviruses: virus-host coevolution among autonomous primate parvoviruses and links between adeno-associated and avian parvoviruses," *J. Virol.* 75: 2729-2740 (2001).
Mushahwar et al., "Molecular and biophysical characterization of TT virus: evidence for a new virus family infecting humans," *Proc Natl. Acad. Sci. USA* 96:3177-3182 (1999).
Nguyen et al., "Identification and characterization of a second novel human erythrovirus variant, A6," *Virology* 301:374-380 (2002).
Okamoto et al., "Species-specific TT viruses in humans and nonhuman primates and their phylogenetic relatedness," *Virology* 277:368-378 (2000).
Okamoto et al., "Genomic characterization of TT viruses (TTVs) in pigs, cats and dogs and their relatedness with species-specific TTVs in primates and tupaias," *J. Gen. Virol.* 83:1291-1297 (2002).
Patou et al., "Characterization of a nested polymerase chain reaction assay for detection of parvovirus B19," *J. Clin. Microbiol.* 31:540-546 (1993).
Schwartz et al., "The canine minute virus (minute virus of canines) is a distinct parvovirus that is most similar to bovine parvovirus," *Virology* 302: 219-223 (2002).
Thom et al., "Distribution of TT virus (TTV), TTV-like minivirus, and related viruses in humans and nonhuman primates," *Virology* 306:324-333 (2003).
GenBank Accession No: AB008394, TT virus genes for ORF2 and ORF1, complete cds.
GenBank Accession No: AB017613, TT virus isolate TUS01 DNA, complete genome.
GenBank Accession No. AB026929, TTV-like mini virus DNA, complete genome, isolate: TLMV-CBD203.
GenBank Accession No. AB026930, TTV-like mini virus DNA, complete genome, isolate: TLMV-CBD231.
GenBank Accession No. AB026931, TTV-like mini virus DNA, complete genome, isolate: TLMV-CBD279.
GenBank Accession No. AB028668, TT virus gene for ORF1 and ORF2, complete genome, isolate:TJN01.
GenBank Accession No. AB028669:TT virus gene for ORF1 and ORF2, complete genome, isolate:TJN02.
GenBank Accession No. AB038626, TTV-like mini virus complete genome, isolate:TLMV-CLC138.
GenBank Accession No. AB038627, TTV-like mini virus complete genome, isolate:TLMV-CLC156.
GenBank Accession No. AB038628, TTV-like mini virus complete genome, isolate:TLMV-CLC205.
GenBank Accession No. AB038629, TTV-like mini virus complete genome, isolate: TLMV-NLC023.
GenBank Accession No: AB038630, TTV-like mini virus complete genome, isolate:TLMV-NLC026.

(Continued)

*Primary Examiner* — Mary E Mosher
(74) *Attorney, Agent, or Firm* — DLA Piper LLP (US)

(57) ABSTRACT

The present invention relates to the discovery of a new human parvovirus, methods of detecting the parvovirus and diagnosing parvovirus infection, methods of treating or preventing parvovirus infection, and methods for identifying anti-parvoviral compounds.

6 Claims, 8 Drawing Sheets

(56) References Cited

OTHER PUBLICATIONS

GenBank Accession No. AB038631, TTV-like mini virus complete genome, isolate: TLMV-NLC030.
GenBank Accession No. AB041957, Torque teno virus DNA, complete genome, isolate: Pt-TTV6.
GenBank Accession No. AB041958, Torque teno virus DNA, complete genome, isolate:Mf-TTV3.
GenBank Accession No. AB041959, Torque teno virus DNA, complete genome, isolate:Mf-TTV9.
GenBank Accession No. AB041960, Torque teno virus DNA, complete genome, isolate: So-TTV2.
GenBank Accession No. AB041961, Torque teno virus DNA, complete genome, isolate: At-TTV3.
GenBank Accession No. AB041962, Torque teno virus DNA, complete genome, isolate: TGP96.
GenBank Accession No. AB041963, Torque teno virus DNA, complete genome, isolate: Pt-TTV8-II.
GenBank Accession No. AB057358, Torque teno virus genes for hypothetical proteins, complete cds, isolate: Tbc-TTV14.
GenBank Accession No. AB076001, Torque teno virus ORF3, ORF2, ORF1 genes, complete cds, isolate: Sd-TTV31.
GenBank Accession No. AB076002, Torque teno virus ORF3, ORF2, ORF1 genes, complete cds, isolate: Cf-TTV10.
GenBank Accession No. AB076003, Torque teno virus ORF3, ORF2, ORF1 genes, complete cds, isolate: Fc-TTV4.
GenBank Accession No. AF122916, TT virus isolate JA1, complete genome.
GenBank Accession No. AF247138, TT virus isolate T3PB, complete genome.
GenBank Accession No. AF291073, TTV-like mini virus isolate PB4TL, complete genome.
GenBank Accession No. AF406966, Bovine parvovirus 2 putative non-structural protein and putative capsid protein genes, complete cds.
GenBank Accession No. AF406967, Bovine parvovirus 3 putative non-structural protein and putative capsid protein genes, complete cds.
GenBank Accession No. AF495467, Minute virus of canines non structural protein 1, NP1, virus protein 1, and virus protein 2 genes, complete cds.
GenBank Accession No. AY064476, Erythrovirus A6 clone c8 non-structural protein, 7.5 kDa protein, capsid protein VP1, and 11 kDa protein genes, complete cds.

* cited by examiner

```
ACGAGGCCTCGTCGCATATGTATTACATCAAAAATTAGCCACGCCCTTCCGGTTCCGGCCACGC
CCTTCCGGTTCCGGTGACGTGCTTCCGGCCACGTCAACTTCCGGCCACGTCAACTTCCGGTGAC
GTATTTCCGCTTCCGGTCCCGCGAAAATTACGTATTTCCGCTTCCGGGACACGTCCGCTTAAAA
GCGGAAGTGACGCCCTTTCCCAACCACACCTACCTCGCCTATAAGAATCAGTGTCAGTTCCTCT
GACTCACTCTGTTCGTAGAGGTCACCATGGACGCTCCTGCCTGGATTGCCGTGCTACAAATTCC
TACTGGATTTCTCTCCAACCCAGCAAACTGGAGGGATTGGGATGGCCTGCAAAGACCCCGCAAT
CTTCTCGCCGACGACTGGCCTATACAGGAGCTCCGTGAGTCTGTTCCATTTTTGACCATGCTG
TTAATTTAGGCTACTGCATATTACAACAGCTGTTTGCCTCGCATGCTGTTACTCTGCCATGCAG
AGTGAAGCCTAGCATGTTTTTGCAGTTAGAACCAAGTAGTGGAGAAGAGAATGAAATGCACTAC
CATTTAGTTGTGAACCAAGCAGACATGGTAGGCAGAGAATGTAGCAACTGGCTGCGCACCTGGA
AAGTCTTTATGGCTGGATATTTGGTAGCTCCTGTGTGGACTTTAAGTTGGAACATTAGAGAAAC
CCGTCAAGGGCGACTATATCAGGCTGATATGAGTTTTGTGAAAAATTACCTGCTACCTAAGCTA
CCACTGAATGATTGCTATTATGCATGGACTAATATAGACAGGTTTGAAGCAGCTGTACTGAGCG
TGCGCAACAGACAGCTTTCAGGTCCTCAAGGTGCTATTGCCTTACCATTCACTGACGCACCTCC
ACGGACACCAGCTGCAGAAGGAGTTCCTCCAACTATGGCAGGAAAAGGAACACAAAGATTCATG
GATCTTATTGACTGGTTAGTTGAAAATGGAATAGCCACAGAAAAGAGGTGGTTATCAGTGAATA
AACTCAGCTACAGGTCCTTTCTAGGAAGCAGTGGTGGAGTTCTTCAAGCAACAAATGCACTACA
AATAGCTAAAAGAGAAATGGTTTTAGCCCACCCTTTATTAAGCTACCTGACAAAGAATGCTTCT
GCTTTTGAAGAAAGTAATAAAGTTGCACAGCTGTTTAGCTTAAATGGCTACAATCCTGTTGACG
CTGCATGGTATTTTGCAGCATGGGCAAGAGGAGTGTGGCCCAAAAGAAGAGCCATATGGCTCTG
GGGCCCAGCTAGTACAGGTAAAACTCTGTTAGCTGCTGCCATAGCAAATCTTAGTCCATCTTAC
GGTTGTGTGAATTGGACAAACCAAAATTTCCCATTTAATGACTGTCACTGTCAAAGCTTAGTGT
GGTGGGAAGAAGGCAGAATGACAGAGAACATTGTTGAAGTAGCCAAAGCTGTGCTTGGTGGAGC
ACCTGTGAGGTTGGATGTAAAGAACAAAGGCAGCGAAGACTACATACCTACCTGTGTCATCATT
ACCTCTAATGGAGATTTAACAGTTACAGTTGATGGCCCTGTGGTTAGCACCCAGCATCAAGAAG
CTTTGCAGACAAGAATAACCATGTTTCAGTTTCAGAGAATGGTTCCGGATGGCTTAGCTCCACT
TCCTGAAGAGGAAGTGAGAAGCTTTTTTAAGCTAGGTGAACAGGAACTGAATATGAAAGGCACA
CCTCCAGAAGAATTTAGAGTGCCAAGAAACTTTGACAAACAACCAATGGCATCTACCAGCAACT
TGCCAAAAGCCTTGTGTGCACCAATGGAAGACAACCAAGTACAATGGATTCTGAAGATGATTG
GTTTCCACCACCCACTCAGAAGAAAAGGCGGGAACTTCAAGAGACACCTCCAACCACTCCCAGT
GAAGTCATTGAGCTGTCCTCTCCGAGTCCATTAGCAGACGCGCCGCCGAGGACACCAGACAGTC
TGGGAGAATTGTCTCTAACTCCTACTTCTGTAAGCCAGATTGTTTCTGCACCATTTCCTGACGA
AACTGCTGAAAGGTATGGAGCTGGGGACATTGAGTCTTTCTGGTCTGAACATGTGTTTGATGCA
GATTGGGCTACAAGGCTACACATTTGTCCCCCAGGTGGTCCTAAACCTTACGGACTTTTTTGGA
CTTACTTATGGTCTCGAGAGTTTTGGAGGTTTAAGCAGAGTCTGAGCCGTTCAGAGGCTCATTT
GATAAATAGAAGATTTATTTGGGCTTGGTGGTAAGTGTGATTTTATGTTTTCTTTGATTTTCTT
GTAGACTTGTTCCTGACGCTGCTACAGGAGCAGAAGACTAACAAGCTTCATTTATTTTTCCAGG
TAAGCAAACATGTCTGCTGCTGATGCTTATCGTCCAGGTGGCAAGCTGCCTCTAGATGAGCTAA
TGCAAAGAATGAATAGAGCAATTCCTGTGGGACCGGAACCTTCAAGTCAAGCCAACCGCGGAGG
GGGGCCATATCAAACTCACTTTGCTATAGGAATAATGTACTCCAAGGCTTTCCAAGGCTTGCTT
AGATTTGCTAATGCTTTACCTCCTGAATTGAGCCCTGTAAAACAGCTTGTTAATCAGTTAGAAA
ATTATAGGCGTAAGACATCTGATACCAGGGTATGGTACAGAGTGTACTTAGACATGACAAGACT
TCTAATTTCTGTGGCTCCTCCAGGAGCAGCAAACAAACTCAGACAGGCAGCAGCAGGTATAACT
CACTCAAAAGCCCCCAATGCTGAAAGCCTGAGAGGCATTGTGCGGTTCGCAGCTGCTGCTTTTG
TACCTACTGTAGAAAATATTGATAGATTTTTTGAAGACTCGCTAACGAACTTTGCCAAAGAAGA
CTTAGACACCTGGCAACAACTCCACGAGCAGTTTATCAAACTCTT
```

FIG. 7

```
TCACCCTCCAGATGTCGGAGTCCACCTTGTTAGTGACAGCCGCGATGAAGGAGCTGATTCCCTT
GTTGAACCAGACCTTGAGCGGCCTGCCGGAGGCGGGCTTACTCTCCCCGGGTATAATTATGTTG
GTCCTGGTAATCCTCTGGATAGTGGTCCCCCTCAGGGACCAGTGGATGAGGCAGCAAAACATCA
TGATGAACGGTACGCAGAGATGATTGAGCATGGGGACATCCCTTATTTACATGGTCACGGCGCT
GACAGATTAATGAACAAAGAGTTAGAAGAAAAGAGCGCCGGGGGGACATTACACACTTAGCAG
ATGTAGTAGTTGGCAATGCTATTAGAGGTTTATGGCAGGCTAAGGAAACTGTTGGTGATATTGC
TGATGTTCAACTTTCTCAGGTCCTACCGCCCGCTCCTCCTTCTTCGGACCAACAACCGGCTTAT
TCCGCAGGAGAGCCCTCAGCCAAGAAGGCGCGGATTGGTACCCCTGACGAGTCTGACCCGGCCT
TGCTTCTGCAGCCTCATACCAATACAATGTCCGTGGAACCAGCTGGAGGAGGAGGTGGAGTTAA
AGTTAAAGCTCAGTGGATAGGTGGAACTAGTTTTTCTGATTCTGTAGTTATTACTTCACATACT
AGAACTTCAATGTTAGCTGATAGAGGGGGGTATGTGCCTGTGTATAAGCAAGGAAGTCATGTAG
ATTCTTCGCAGCCTGTAATGGGTATGAAAACACCTTATTCTTACATTGATGTTAATGCTTTATC
TGCTCATTTTACTCCTAGAGACTTTCAGCAACTGCTAGATGAATATGATGAAATTAAACCTAAA
AGCTTAACTATTGCAATTTCTGCTATTGTAATTAAGGATGTTGCAACCAATCAAACAGGTACTA
CTGTTTCTGATTCTGCAAGTGGTGGGATTACTGTATTTGCTGATGATAGCTATGACTATCCATA
TGTATTAGGTCATAATCAAGATACATTACCAGGTCATTTACCAGGAGAAAATTATGTATTGCCT
CAGTATGGGTACATTACAAGAGGCAGAGAAATTGATCAACAGAACAGCATTGTAGCTATTAGTG
ATCATAAGACAGAACTGTTTTTTTTAGAGCACCATGATGCAGAGTGTTTGGGTACAGGAGATCA
CTGGTCTCATCACTATGAGTTTCCAGATGACCTACCTTGGAGAAAATTGTCAACTCCCAACCAA
ACATTGTATGCAAGACATAATCCAATTCCTTCTAGCAGGTTAGCTATTATGACAGGTGTTGATA
ATGATGGGACTGCCATTTGGAAACGCCCTGAAGGCATGGATGTTGGCAGACTCCCATTAAATTA
TGTTCCAGGGCCAGCTCTAATGATGCCAACAGACACCCAAATTAGAAACACAACTTTCAGAGAT
CCTGTGGCTATTGGAAATCCTGCTACAAGTGACAGGTATAGTGTAGCTCCTTTAGTCCATCAAC
CATGGTCTGTCCGTACAGAAGAATGGCTAGCAAACAAAACAGACTATGCTGTTCATAATTATTT
AGGAGGTGTTGCATACACTAGAAGAAAGCATGAAGAGTCTTATGATAAACATGAGGAGGACCGA
GATGGTAGAGTTACTAACCCATCCAGAGTTGTTCAGATAGATGGTGATTTAGCAGCTCCTCATG
TGGGTCACACGTTTTTTGTTCCTGGACACACCAGAGTTACCTCTGGTGGTACTGATACAGTGTA
CAGCCCAAAATTATATCAGGAACCTGTGTTTCCTTTGTTTCCTGGTGCTGTTTGGAACCCAAAT
CCTTTATCATATGATTGCCAAATATGGACTAAAATTCCTAATACAGAATGTCATTTTTTGCTC
AATATCCTCTTTTGGGAGGTTGGGGAGTTCTTACTCCTCCTCCAATGATTTTTGTGAAGCTCAG
GTCACAACCAGGCCCTCCTAGTCCAGGTGCTCACACAGTTCCACAATCTAATTTAAACCAGTAT
GCAATTTTTCACTTGCATTATAGTATGCAGTTTTTAGTTAAGCGCCGCAAGAGATCTCGCCGCC
ATAATCCCGAGAAACCTGCTCCTTTCCCGACAACAGATTCGGGACGTATGCCTTTTACCCTTGC
CAATAGCTTAAAAGACCCCAATACACCAGTGTATGAAGTGCCTTCTGATCAATGGATTGCGCGA
AATTATTCTCATTTGCTGTAATAAATTTATAAAATTTCATTGCTGTGAGACTGATTCTTATAGG
CGAGGTAGGTGTGGTTGGGAAAGGGCGTCACTTCCGCTTTTAAGCGGACGTGTCCCGGAAGCGG
AAATACGCAATTTTCGCGGGACCGGAAGCGGAAATACGC
```

FIG. 7 (CONT.)

SEQUENCE LISTING

<160> NUMBER OF SEQ ID NOS: 14

<210> SEQ ID NO 1
<211> LENGTH: 5268
<212> TYPE: DNA
<213> ORGANISM: Parvovirus HP-4 (PARV4)
<220> FEATURE:
<223> OTHER INFORMATION: human parvovirus HP-4 (PARV4) genomic sequence
<220> FEATURE:
<221> NAME/KEY: CDS
<222> LOCATION: (283)..(2274)
<223> OTHER INFORMATION: open reading frame #1 (ORF #1)
<220> FEATURE:
<221> NAME/KEY: CDS
<222> LOCATION: (2378)..(5122)
<223> OTHER INFORMATION: open reading frame #2 (ORF #2)

<400> SEQUENCE: 1

```
acgaggcctc gtcgcatatg tattacatca aaaattagcc acgcccttcc ggttccggcc      60
acgcccttcc ggttccggtg acgtgcttcc ggccacgtca acttccggcc acgtcaactt     120
ccggtgacgt atttccgctt ccggtcccgc gaaaattacg tatttccgct tccgggacac     180
gtccgcttaa aagcggaagt gacgcccttt cccaaccaca cctacctcgc ctataagaat     240
cagtgtcagt tcctctgact cactctgttc gtagaggtca ccatggacgc tcctgcctgg     300
attgccgtgc tacaaattcc tactggattt ctctccaacc cagcaaactg gagggattgg     360
gatggcctgc aaagaccccg caatcttctc gccgacgact ggcctataca ggagctccgt     420
gagtctgttc cattttttga ccatgctgtt aatttaggct actgcatatt acaacagctg     480
tttgcctcgc atgctgttac tctgccatgc agagtgaagc ctagcatgtt tttgcagtta     540
gaaccaagta gtggagaaga gaatgaaatg cactaccatt tagttgtgaa ccaagcagac     600
atggtaggca gagaatgtag caactggctg cgcacctgga agtctttat ggctggatat     660
ttggtagctc ctgtgtggac tttaagttgg aacattagag aaacccgtca agggcgacta     720
tatcaggctg atatgagttt tgtgaaaaat tacctgctac ctaagctacc actgaatgat     780
tgctattatg catggactaa tatagacagg tttgaagcag ctgtactgag cgtgcgcaac     840
agacagcttt caggtcctca aggtgctatt gccttaccat tcactgacgc acctccacgg     900
acaccagctg cagaaggagt tcctccaact atggcaggaa aaggaacaca aagattcatg     960
gatcttattg actggttagt tgaaaatgga atagccacag aaaagaggtg gttatcagtg    1020
aataaactca gctacaggtc ctttctagga agcagtggtg gagttcttca agcaacaaat    1080
gcactacaaa tagctaaaag agaaatggtt ttagcccacc ctttattaag ctacctgaca    1140
aagaatgctt ctgcttttga agaaagtaat aaagttgcac agctgtttag cttaaatggc    1200
tacaatcctg ttgacgctgc atggtatttt gcagcatggg caagaggagt gtggcccaaa    1260
agaagagcca tatggctctg ggcccagct agtacaggta aaactctgtt agctgctgcc    1320
atagcaaatc ttagtccatc ttacggttgt gtgaattgga caaaccaaaa tttcccattt    1380
aatgactgtc actgtcaaag cttagtgtgg tgggaagaag cagaatgac agagaacatt    1440
gttgaagtag ccaaagctgt gcttggtgga gcacctgtga ggttggatgt aaagaacaaa    1500
ggcagcgaag actacatacc tacctgtgtc atcattacct ctaatggaga tttaacagtt    1560
acagttgatg gcctgtggt tagcacccag catcaagaag ctttgcagac aagaataacc    1620
atgtttcagt tcagagaat ggttccggat ggcttagctc cacttcctga agaggaagtg    1680
agaagctttt ttaagctagg tgaacaggaa ctgaatatga aaggcacacc tccagaagaa    1740
```

```
tttagagtgc caagaaactt tgacaaacaa ccaatggcat ctaccagcaa cttgccaaaa    1800
gccttgtgtg caccaatgga agacaaccaa gtacaatggg attctgaaga tgattggttt    1860
ccaccaccca ctcagaagaa aaggcgggaa cttcaagaga cacctccaac cactcccagt    1920
gaagtcattg agctgtcctc tccgagtcca ttagcagacg cgccgccgag gacaccagac    1980
agtctgggag aattgtctct aactcctact tctgtaagcc agattgtttc tgcaccattt    2040
cctgacgaaa ctgctgaaag gtatggagct ggggacattg agtctttctg gtctgaacat    2100
gtgtttgatg cagattgggc tacaaggcta cacatttgtc ccccaggtgg tcctaaacct    2160
tacggacttt tttggactta cttatggtct cgagagtttt ggaggtttaa gcagagtctg    2220
agccgttcag aggctcattt gataaataga agatttattt gggcttggtg gtaagtgtga    2280
ttttatgttt tcttttgattt tcttgtagac ttgttcctga cgctgctaca ggagcagaag    2340
actaacaagc ttcatttatt tttccaggta agcaaacatg tctgctgctg atgcttatcg    2400
tccaggtggc aagctgcctc tagatgagct aatgcaaaga atgaatagag caattcctgt    2460
gggaccggaa ccttcaagtc aagccaaccg cggagggggg ccatatcaaa ctcactttgc    2520
tataggaata atgtactcca aggctttcca aggcttgctt agatttgcta atgctttacc    2580
tcctgaattg agccctgtaa aacagcttgt taatcagtta gaaaattata ggcgtaagac    2640
atctgatacc agggtatggt acagagtgta cttagacatg acaagacttc taatttctgt    2700
ggctcctcca ggagcagcaa acaaactcag acaggcagca gcaggtataa ctcactcaaa    2760
agcccccaat gctgaaagcc tgagaggcat tgtgcggttc gcagctgctg cttttgtacc    2820
tactgtagaa aatattgata gatttttga agactcgcta acgaactttg ccaaagaaga    2880
cttagacacc tggcaacaac tccacgagca gtttatcaaa ctctttcacc ctccagatgt    2940
cggagtccac cttgttagtg acagccgcga tgaaggagct gattcccttg ttgaaccaga    3000
ccttgagcgg cctgccggag gcgggcttac tctccccggg tataattatg ttggtcctgg    3060
taatcctctg gatagtggtc cccctcaggg accagtggat gaggcagcaa acatcatga    3120 tgaacggtac gcagagatga ttgagcatgg ggacatccct tatttacatg gtcacggcgc    3180
tgacagatta atgaacaaag agttagaaga aaaagagcgc cggggggaca ttacacactt    3240
agcagatgta gtagttggca atgctattag aggtttatgg caggctaagg aaactgttgg    3300
tgatattgct gatgttcaac tttctcaggt cctaccgccc gctcctcctt cttcggacca    3360
acaaccggct tattccgcag gagagccctc agccaagaag gcgcggattg gtaccctga    3420 cgagtctgac ccgccttgc ttctgcagcc tcataccaat acaatgtccg tggaaccagc    3480
tggaggagga ggtggagtta agttaaagc tcagtggata ggtggaacta gttttttctga    3540 ttctgtagtt attacttcac atactagaac ttcaatgtta gctgatagag ggggtatgt    3600 gcctgtgtat aagcaaggaa gtcatgtaga ttcttcgcag cctgtaatgg gtatgaaaac    3660 acccttattct tacattgatg ttaatgcttt atctgctcat tttactccta gagactttca    3720
gcaactgcta gatgaatatg atgaaattaa acctaaaagc ttaactattg caatttctgc    3780
tattgtaatt aaggatgttg caaccaatca aacaggtact actgtttctg attctgcaag    3840
tggtgggatt actgtatttg ctgatgatag ctatgactat ccatatgtat taggtcataa    3900
tcaagataca ttaccaggtc atttaccagg agaaaattat gtattgcctc agtatgggta    3960
cattacaaga ggcagagaaa ttgatcaaca gaacagcatt gtagctatta gtgatcataa    4020
gacagaactg ttttttttag agcaccatga tgcagagtgt ttgggtacag gagatcactg    4080
gtctcatcac tatgagtttc cagatgacct accttggaga aaattgtcaa ctcccaacca    4140
```

```
aacattgtat gcaagacata atccaattcc ttctagcagg ttagctatta tgacaggtgt    4200
tgataatgat gggactgcca tttggaaacg ccctgaaggc atggatgttg cagactccc     4260 attaaattat gttccagggc cagctctaat gatgccaaca gacacccaaa ttagaaacac    4320
aactttcaga gatcctgtgg ctattggaaa tcctgctaca agtgacaggt atagtgtagc    4380
tcctttagtc catcaaccat ggtctgtccg tacagaagaa tggctagcaa acaaaacaga    4440
ctatgctgtt cataattatt taggaggtgt tgcatacact agaagaaagc atgaagagtc    4500
ttatgataaa catgaggagg accgagatgg tagagttact aacccatcca gagttgttca    4560
gatagatggt gatttagcag ctcctcatgt gggtcacacg ttttttgttc ctggacacac    4620
cagagttacc tctggtggta ctgatacagt gtacagccca aaattatatc aggaacctgt    4680
gtttcctttg tttcctggtg ctgttttgaa cccaaatcct ttatcatatg attgccaaat    4740
atggactaaa attcctaata cagaatgtca ttttttttgct caatatcctc ttttgggagg    4800
ttggggagtt cttactcctc ctccaatgat ttttgtgaag ctcaggtcac aaccaggccc    4860
tcctagtcca ggtgctcaca cagttccaca atctaattta aaccagtatg caattttttca    4920 cttgcattat agtatgcagt ttttagttaa gcgccgcaag agatctcgcc gccataatcc    4980
cgagaaacct gctcctttcc cgacaacaga ttcgggacgt atgcctttta cccttgccaa    5040
tagcttaaaa gaccccaata caccagtgta tgaagtgcct tctgatcaat ggattgcgcg    5100
aaattattct catttgctgt aataaattta taaaatttca ttgctgtgag actgattctt    5160
ataggcgagg taggtgtggt tgggaaaggg cgtcacttcc gcttttaagc ggacgtgtcc    5220
cggaagcgga aatacgcaat tttcgcggga ccggaagcgg aaatacgc                 5268
```

<210> SEQ ID NO 2
<211> LENGTH: 1992
<212> TYPE: DNA
<213> ORGANISM: Parvovirus HP-4 (PARV4)
<220> FEATURE:
<223> OTHER INFORMATION: open reading frame #1 (ORF #1)

<400> SEQUENCE: 2

```
atggacgctc ctgcctggat tgccgtgcta caaattccta ctggatttct ctccaaccca     60
gcaaactgga gggattggga tggcctgcaa agaccccgca atcttctcgc cgacgactgg    120
cctatacagg agctccgtga gtctgttcca ttttttgacc atgctgttaa tttaggctac    180
tgcatattac aacagctgtt tgcctcgcat gctgttactc tgccatgcag agtgaagcct    240
agcatgtttt tgcagttaga accaagtagt ggagaagaga atgaaatgca ctaccattta    300
gttgtgaacc aagcagacat ggtaggcaga gaatgtagca actggctgcg cacctggaaa    360
gtctttatgg ctggatattt ggtagctcct gtgtggactt aagttggaa cattagagaa    420 acccgtcaag ggcgactata tcaggctgat atgagttttg tgaaaaatta cctgctacct    480
aagctaccac tgaatgattg ctattatgca tggactaata tagacaggtt tgaagcagct    540
gtactgagcg tgcgcaacag acagctttca ggtcctcaag gtgctattgc cttaccattc    600
actgacgcac ctccacggac accagctgca gaaggagttc ctccaactat ggcaggaaaa    660
ggaacacaaa gattcatgga tcttattgac tggttagttg aaaatggaat agccacagaa    720
aagaggtggt tatcagtgaa taaactcagc tacaggtcct ttctaggaag cagtggtgga    780
gttcttcaag caacaaatgc actacaaata gctaaaagag aaatggtttt agcccaccct    840
ttattaagct acctgacaaa gaatgcttct gctttttgaag aaagtaataa agttgcacag    900
ctgtttagct taaatggcta caatcctgtt gacgctgcat ggtattttgc agcatgggca    960
```

-continued

```
agaggagtgt ggcccaaaag aagagccata tggctctggg gcccagctag tacaggtaaa    1020
actctgttag ctgctgccat agcaaatctt agtccatctt acggttgtgt gaattggaca    1080
aaccaaaatt tcccatttaa tgactgtcac tgtcaaagct tagtgtggtg ggaagaaggc    1140
agaatgacag agaacattgt tgaagtagcc aaagctgtgc ttggtggagc acctgtgagg    1200
ttggatgtaa agaacaaagg cagcgaagac tacatacctg cctgtgtcat cattacctct    1260 aatgagatt  taacagttac agttgatggc cctgtggtta gcacccagca tcaagaagct    1320
ttgcagacaa gaataaccat gtttcagttt cagagaatgg ttccggatgg cttagctcca    1380
cttcctgaag aggaagtgag aagcttttt  aagctaggtg aacaggaact gaatatgaaa    1440
ggcacacctc cagaagaatt tagagtgcca agaaactttg acaaacaacc aatggcatct    1500
accagcaact tgccaaaagc cttgtgtgca ccaatggaag acaaccaagt acaatgggat    1560
tctgaagatg attggtttcc accacccact cagaagaaaa ggcgggaact tcaagagaca    1620
cctccaacca ctcccagtga agtcattgag ctgtcctctc cgagtccatt agcagacgcg    1680
ccgccgagga caccagacag tctgggagaa ttgtctctaa ctcctacttc tgtaagccag    1740
attgtttctg caccatttcc tgacgaaact gctgaaaggt atggagctgg ggacattgag    1800
tctttctggt ctgaacatgt gtttgatgca gattgggcta caaggctaca catttgtccc    1860
ccaggtggtc ctaaaccttg cggacttttt tggacttact tatggtctcg agagttttgg    1920
aggtttaagc agagtctgag ccgttcagag gctcatttga taaatagaag atttatttgg    1980
gcttggtggt aa                                                       1992
```

<210> SEQ ID NO 3
<211> LENGTH: 2745
<212> TYPE: DNA
<213> ORGANISM: Parvovirus HP-4 (PARV4)
<220> FEATURE:
<223> OTHER INFORMATION: open reading frame #2 (ORF #2)

<400> SEQUENCE: 3

```
atgtctgctg ctgatgctta tcgtccaggt ggcaagctgc ctctagatga gctaatgcaa      60
agaatgaata gagcaattcc tgtgggaccg gaaccttcaa gtcaagccaa ccgcggaggg     120
gggccatatc aaactcactt tgctatagga ataatgtact ccaaggcttt ccaaggcttg     180
cttagatttg ctaatgcttt acctcctgaa ttgagccctg taaaacagct tgttaatcag     240
ttagaaaatt ataggcgtaa gacatctgat accagggtat ggtacagagt gtacttagac     300
atgacaagac ttctaatttc tgtggctcct ccaggagcag caaacaaact cagacaggca     360
gcagcaggta taactcactc aaaagccccc aatgctgaaa gcctgagagg cattgtgcgg     420
ttcgcagctg ctgcttttgt acctactgta gaaaatattg atagatttt  tgaagactcg     480 ctaacgaact tgccaaagga agacttagac acctggcaac aactccacga gcagtttatc     540
aaactctttc accctccaga gtcggagtc accttgtta  gtgacagccg cgatgaagga     600
gctgattccc ttgttgaacc agaccttgag cggcctgccg gaggcgggct tactctcccc     660
gggtataatt atgttggtcc tggtaatcct ctggatagtg gtccccctca gggaccagtg     720
gatgaggcag caaacatca  tgatgaacgg tacgcagaga tgattgagca tggggacatc     780
ccttatttac atggtcacgg cgctgacaga ttaatgaaca aagagttaga agaaaaagag     840
cgccgggggg acattacaca cttagcagat gtagtagttg gcaatgctat tagaggttta     900
tggcaggcta aggaaactgt tggtgatatt gctgatgttc aactttctca ggtcctaccg     960
cccgctcctc cttcttcgga ccaacaaccg gcttattccg caggagagcc ctcagccaag    1020
```

```
aaggcgcgga ttggtacccc tgacgagtct gacccggcct tgcttctgca gcctcatacc      1080
aatacaatgt ccgtggaacc agctggagga ggaggtggag ttaaagttaa agctcagtgg      1140
ataggtggaa ctagttttc tgattctgta gttattactt cacatactag aacttcaatg      1200
ttagctgata gagggggta tgtgcctgtg tataagcaag gaagtcatgt agattcttcg      1260
cagcctgtaa tgggtatgaa acaccttat tcttacattg atgttaatgc tttatctgct      1320
cattttactc ctagagactt tcagcaactg ctagatgaat atgatgaaat taaacctaaa      1380
agcttaacta ttgcaatttc tgctattgta attaaggatg ttgcaaccaa tcaaacaggt      1440
actactgttt ctgattctgc aagtggtggg attactgtat ttgctgatga tagctatgac      1500
tatccatatg tattaggtca taatcaagat acattaccag gtcatttacc aggagaaaat      1560
tatgtattgc ctcagtatgg gtacattaca agaggcagaa aaattgatca acagaacagc      1620
attgtagcta ttagtgatca taagacagaa ctgtttttt tagagcacca tgatgcagag      1680
tgtttgggta caggagatca ctggtctcat cactatgagt ttccagatga cctaccttgg      1740
agaaaattgt caactcccaa ccaaacattg tatgcaagac ataatccaat tccttctagc      1800
aggttagcta ttatgacagg tgttgataat gatgggactg ccatttggaa acgccctgaa      1860
ggcatggatg ttggcagact cccattaaat tatgttccag ggccagctct aatgatgcca      1920
acagacaccc aaattagaaa cacaactttc agagatcctg tggctattgg aaatcctgct      1980
acaagtgaca ggtatagtgt agctccttta gtccatcaac catggtctgt ccgtacagaa      2040
gaatggctag caaacaaaac agactatgct gttcataatt atttaggagg tgttgcatac      2100
actagaagaa agcatgaaga gtcttatgat aaacatgagg aggaccgaga tggtagagtt      2160
actaacccat ccagagttgt tcagatagat ggtgatttag cagctcctca tgtgggtcac      2220
acgttttttg ttcctggaca caccagagtt acctctggtg gtactgatac agtgtacagc      2280
ccaaaattat atcaggaacc tgtgtttcct ttgtttcctg gtgctgtttg gaacccaaat      2340
cctttatcat atgattgcca aatatggact aaaaattcta atacagaatg tcatttttt       2400 gctcaatatc ctctttggg aggttgggga gttcttactc ctcctccaat gatttttgtg       2460
aagctcaggt cacaaccagg ccctcctagt ccaggtgctc acacagttcc acaatctaat      2520
ttaaaccagt atgcaatttt tcacttgcat tatagtatgc agtttttagt taagcgccgc      2580
aagagatctc gccgccataa tcccgagaaa cctgctcctt cccgacaac agattcggga       2640 cgtatgcctt ttacccttgc caatagctta aaagacccca atacaccagt gtatgaagtg      2700
ccttctgatc aatggattgc gcgaaattat tctcatttgc tgtaa                      2745
```

<210> SEQ ID NO 4
<211> LENGTH: 200
<212> TYPE: PRT
<213> ORGANISM: Artificial Sequence
<220> FEATURE:
<223> OTHER INFORMATION: Description of Artificial Sequence:poly Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 4

Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly
             20                  25                  30

-continued

Gly Gly Gly Gly Gly Gly Gly Gly Gly Gly Gly Gly
            35                  40                  45

Gly Gly Gly Gly Gly Gly Gly Gly Gly Gly Gly Gly
    50                  55                  60

Gly Gly Gly Gly Gly Gly Gly Gly Gly Gly Gly Gly Gly
65                  70                  75                  80

Gly Gly Gly Gly Gly Gly Gly Gly Gly Gly Gly Gly
            85                  90                  95

Gly Gly Gly Gly Gly Gly Gly Gly Gly Gly Gly Gly
        100                 105                 110

Gly Gly Gly Gly Gly Gly Gly Gly Gly Gly Gly Gly
    115                 120                 125

Gly Gly Gly Gly Gly Gly Gly Gly Gly Gly Gly Gly
130                 135                 140

Gly Gly Gly Gly Gly Gly Gly Gly Gly Gly Gly Gly Gly
145                 150                 155                 160

Gly Gly Gly Gly Gly Gly Gly Gly Gly Gly Gly Gly
            165                 170                 175

Gly Gly Gly Gly Gly Gly Gly Gly Gly Gly Gly Gly
        180                 185                 190

Gly Gly Gly Gly Gly Gly Gly Gly
    195                 200

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      oligonucleotide adaptor NBam24

<400> SEQUENCE: 5
aggcaactgt gctatccgag ggag                                          24

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence:
      oligonucleotide adaptor NCsp11

<400> SEQUENCE: 6
tactccctcg g                                                        11

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:HP-4 PCR
      amplification primer pr-3B-04303-46F

<400> SEQUENCE: 7
tgccttacca ttcactgacg c                                             21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:HP-4 PCR
      amplification primer pr-7R-04303-174R

<400> SEQUENCE: 8
ttggcaaggg taaaaggcat                                               20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:HP-4
      specific linear amplification primer pr4303-377R

<400> SEQUENCE: 9
actccttctg cagctggtgt c                                             21

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:anchor
      abridged primer for 5' region amplification
<220> FEATURE:
<221> NAME/KEY: modified_base
<222> LOCATION: (24)..(25)
<223> OTHER INFORMATION: i
<220> FEATURE:
<221> NAME/KEY: modified_base
<222> LOCATION: (29)..(30)
<223> OTHER INFORMATION: i

<400> SEQUENCE: 10
ggccacgcgt cgactagtac gggnngggnn gggttg                             36

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:small
      anellovirus 1 (SAV-1) PCR amplification primer
      prSAV-1-IF-784F

<400> SEQUENCE: 11
gtggcgaatg gctgagttta ccy                                           23

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:small
      anellovirus 1 (SAV-1) PCR amplification primer
      prSAV-1-IR-988R

<400> SEQUENCE: 12
gtgttggtgt ctgtaaaagg tcataacac                                     29

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:small
      anellovirus 2 (SAV-2) PCR amplification primer
      pr5412-2201
<220> FEATURE:
<221> NAME/KEY: modified_base
<222> LOCATION: (3)..(5)
<223> OTHER INFORMATION: n = g, a, c or t

```
<400> SEQUENCE: 13
gtnnngaatg gctgagttta cy                                              22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:small
      anellovirus 2 (SAV-2) PCR amplification primer
      pr5412-97

<400> SEQUENCE: 14
tcttcttacc ttgtaccggc g                                               21
```

HUMAN PARVOVIRUS

CROSS-REFERENCES TO RELATED APPLICATIONS

This application is a U.S. National Phase Application, filed under 35 U.S.C. §371, of Patent Cooperation Treaty Application Number PCT/US2005/018314, filed May 24, 2005, which claims the benefit of U.S. Provisional Application No. 60/574,430, filed May 24, 2004. Each of the aforementioned applications are herein incorporated by reference for all purposes.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to the discovery of a new human parvovirus, methods of detecting the parvovirus and diagnosing parvovirus infection, methods of treating or preventing parvovirus infection, and methods for identifying anti-parvoviral compounds.

BACKGROUND OF THE INVENTION

Parvoviruses are among the smallest DNA-containing viruses that infect animals and man. The parvoviridae family is divided into three genera: *Parvovirus; Dependovirus* (adeno-associated); and *Densovirus. Parvoviruses* range in size from 15 to 28 nm in diameter, lack a lipid membrane (non-enveloped), and contain a single strand of DNA. *Parvoviruses* are heat stable and generally resistant to chemical deactivating agents, which may account for their prevalence and persistence in the environment. In animals, many diseases such as canine parvovirus and feline panleukopenia exhibit high morbidity and high mortality in affected animal populations and the infections can persist endemically.

In humans, the first identified pathogenic member of this family is parvovirus B19, which is a member of genus erythrovirus. Other B19-related human parvoviruses include A6 and V9 (see, e.g., Ngyen et al. "Identification and characterization of a second novel human erythrovirus variant, A6." Virology. 2002 Sep. 30; 301(2):374-80). The genomes of A6 and V9 are highly related to that of B19. Animal parvoviruses such as canine parvovirus, feline parvovirus, mink enteritis virus, and porcine parvovirus, are responsible for many serious diseases in animals. As with other parvoviruses, B19 is highly contagious and exhibits high morbidity in affected populations. B19 causes fifth disease in normal individuals, transient aplastic crisis in patients with underlying hemolysis, and chronic anemia due to persistent infection in immunocompromised patients. B19 infection in pregnancy can lead to hydrops fetalis and fetal loss. B19 has also been implicated as the cause of chronic arthritis in adults where there is evidence of recent B19 infection, e.g., rheumatoid and inflammatory arthritis.

Despite the known pathogenicity of parvoviruses and the urgent need for methods to prevent, diagnose and treat parvovirus infections, other human parvoviruses have not yet been identified. Therefore a need exists to identify human parvoviruses and to provide a method for diagnosing, preventing and treating parvovirus infection. Moreover, there exists a need to provide methods to detect, purify and/or remove parvoviruses from samples such as human blood products.

BRIEF SUMMARY OF THE INVENTION

The present invention identifies, for the first time, a new human parvovirus HP-4. Also identified is the genomic sequence of the virus, and open-reading frames encoding viral proteins. The present invention therefore provides methods of detecting the parvovirus and diagnosing parvovirus infection, methods of treating or preventing parvovirus infection, and methods for identifying anti-parvoviral compounds.

BRIEF DESCRIPTION OF THE DRAWINGS

FIG. 7: Nucleotide sequence of new human parvovirus (SEQ ID NO:1) with ORF #1 (SEQ ID NO:2) and ORF #2 (SEQ ID NO:3) underlined.

DETAILED DESCRIPTION OF THE INVENTION

Introduction

Figure 1A:
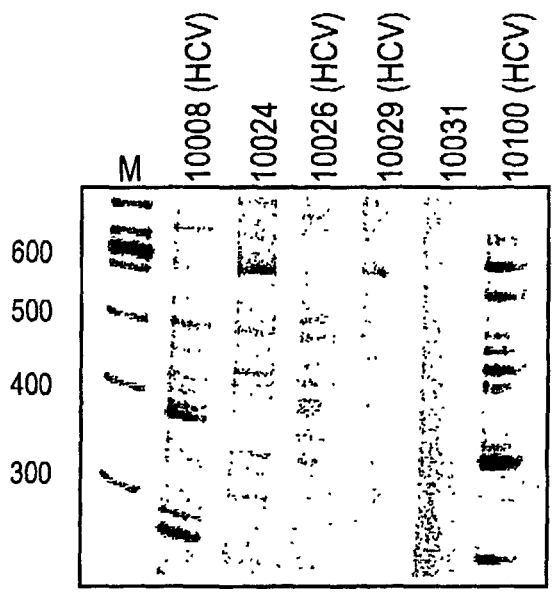
FIG. 1A-C. DNAse-SISPA amplification products from (A) Six HCV positive plasma samples used to test methodology, (B) Three RNA-extracted plasma samples and (C) three DNA extracted plasma samples. PCR products were analyzed on a 6.5% polyacrylamide gel. Viral sequences identified are shown in brackets. M indicates molecular weight markers.

The development of various molecular methods for that task including immunoreactive cDNA expression library screening, representational difference analysis (RDA), DNA microarrays and use of degenerate PCR primers have resulted in the identification of numerous human viruses including hepatitis C virus (HCV) (Choo et al., *Science* 244, 359-361 (1989)), *Human herpes virus* 8 (HHV-8) (Chang et al., *Science* 266, 1865-9 (1994)), the SARS coronavirus (Wang et al., *PLoSBiol* 1, E2 (2003)), GBV-C/HGV (Simons et al., *Proc Natl Acad Sci USA* 92, 3401-5 (1995); Linnen et al., *Science* 271, 505-8 (1996)), hantavirus (Nichol et al., *Science* 262, 914-7 (1993)) and TTV (Nishizawa et al., *Biochem Biophys*

Res Commun 241, 92-7 (1997); Mushahwar et al., *Proc Natl Acad Sci USA* 96, 3177-82 (1999)) and herpes viruses in monkeys (Rose et al., *J Virol* 71, 4138-44 (1997); Greensill et al., *J Virol* 74, 1572-7 (2000)).

Allander et al. recently reported on a method for the sequence independent single primer amplification of nucleic acids in serum (DNase-SISPA) (Allander et al, T., *Proc Natl Acad Sci USA* 98, 11609-14 (2001)). This method first removes contaminating human DNA in plasma or serum by DNase digestion. Viral nucleic acids protected from DNase digestion by their viral coats are then converted into double stranded DNA (dsDNA) using random primers. The dsDNA is then digested by a 4 base pair specific restriction endonuclease resulting in two overhanging bases to which are ligated a complementary oligonucleotide linker. A PCR primer complementary to the ligated linker is then used to PCR amplify the sequences between the restriction sites. The PCR products are analyzed by PAGE and distinct DNA bands are extracted, subcloned and sequenced. Similarity to known viruses is then tested using BLASTn (for nucleic acid similarity) and tBLASTx (for protein similarity) (Allander et al., T., *Proc Natl Acad Sci USA* 98, 11609-14 (2001)).

The DNase-SISPA method does not require foreknowledge of the viral sequences being amplified and can therefore theoretically amplify more divergent members of known viral families than nucleic acid sequence similarity-dependent approaches using degenerate primers (Ehlers et al., *J Virol* 77, 10695-9 (2003); Culley et al., *Nature* 424, 1054-7 (2003)) or microarrays (Wang et al., *PLoSBiol* 1, E2 (2003); Wang et al., *Proc Natl Acad Sci USA* 99, 15687-92 (2002)). DNase-SISPA is more closely related to the non-specific linker amplified shotgun library sequencing method recently used to identify viruses in sea water and human feces (Breitbart et al., *Proc Natl Acad Sci USA* 99, 14250-5 (2002); Breitbart et al., *J Bacteriol* 185, 6220-3 (2003)).

DNase-SISPA was used in the present application to determine if known and previously uncharacterized viruses could be identified in the plasma samples of 25 patients suffering from acute viral infection syndrome. GBV-C/HGV was identified in three and HBV in one individual. Furthermore, three previously un-described DNA viruses were also detected, a parvovirus (HP-4) and two viruses related to TT Virus (TTV). Plasma nucleic acids distantly related to bacterial sequences or with no detectable similarities to known sequences were also detected. Complete viral genome sequencing and phylogenetic analysis confirmed the presence of a new parvovirus distinct from known human and animal parvoviruses, and of two related TTV-like viruses highly divergent from both the TTV and TTV-like minivirus groups. The detection of 2 previously un-described viral species in a small group of individuals presenting acute viral syndrome with unknown etiology suggests that numerous human viruses may still remain unidentified.

Figure 3:
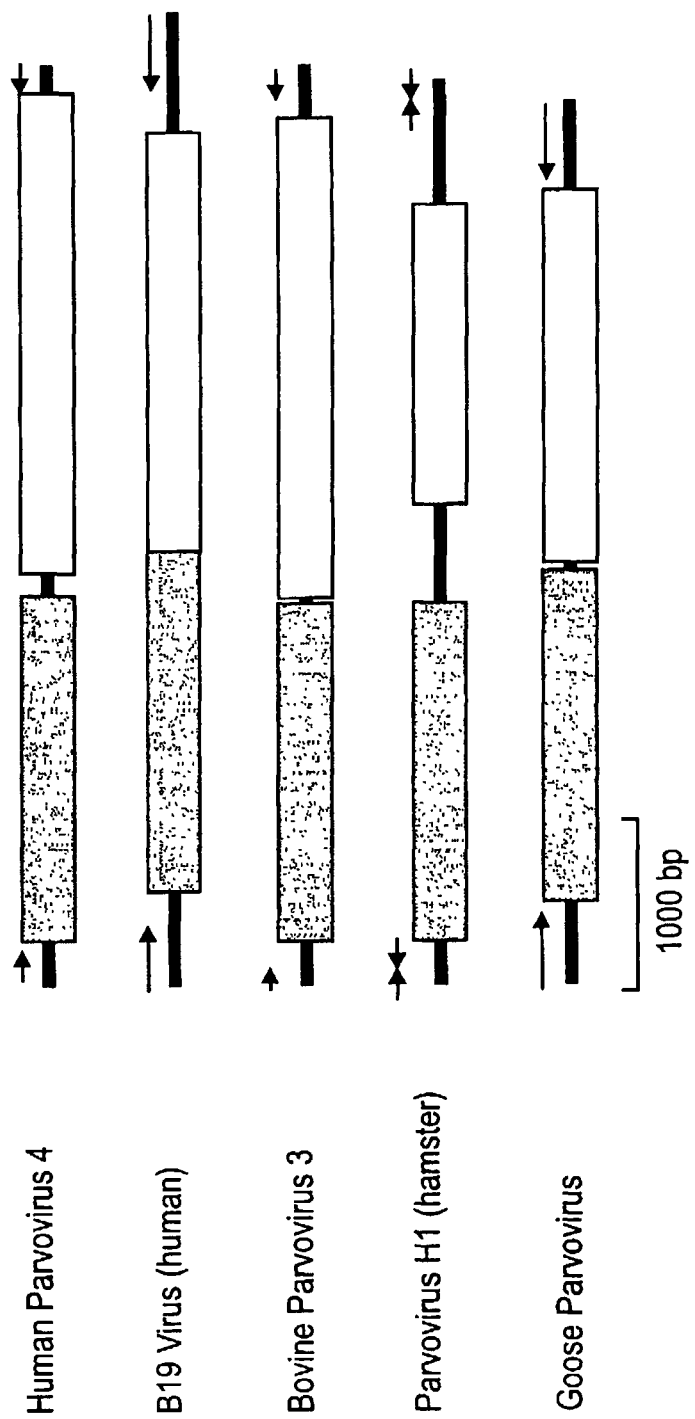
FIG. 3. The genetic organization of HP-4 compared to B19, BVP-3, Parvovirus H1, and Goose Parvoviruses. The gray and white boxes represent the genes encoding for nonstructural and structural proteins respectively. The arrows indicate the position of the terminal repeat sequences. The arrows at the extremities of Parvovirus H1 denote that the terminal repeat sequences are dissimilar.

In one embodiment, the present invention provides a new human parvovirus, HP-4, as well as the genomic sequence of the virus and open reading frames encoding viral proteins. HP-4 is also referred to as PARV4. The results described herein indicate that HP-4 is a unique member of the Parvoviridae family that is not closely related by sequence identity to any other known human or animal parvovirus (see, e.g., FIG. 4). The virus contains a single stranded DNA genome which replicates in the cell nucleus, and which encodes the structural proteins of the virus and non-structural proteins involved in viral replication. Parvoviruses are not enveloped and form icosohedral capsids. The genome of parvoviruses typically encodes open reading frames encoding both structural (e.g., two to three capsid proteins) and a non-structural proteins (e.g., one to four proteins or more involved in, e.g., viral replication, gene expression, and capsid synthesis). The proteins are produced from the open reading frames via alternative slicing or polyprotein processing. The structural and non-structural proteins encoded by the two HP-4 ORFs are easily identified by alignment to other parvovirus sequences, e.g., B19 (see, e.g., FIG. 3).

Symptoms associated with HP-4 infection include cold-like symptoms or symptoms of an acute viral illness, including fatigue, night sweats, phyrangitis, myalgia, arthralgia, neck stiffness, vomiting diarrhea, and confusion. Some or all symptoms, in varying degree, may be present in an HP-4 infection. Typically, parvovirus infections are transmitted via a respiratory route, through blood-derived products, transfusion and from mother to fetus. Parvoviruses are typically highly contagious and can infect the general human population. Subjects at risk for infection also include immunocompromised subjects, pregnant woman, transfusion patients, intravenous drug users, and subjects taking using blood derived products.

The identification of the new HP-4 virus provides methods of detecting the virus, its genome, transcripts, and proteins encoding structural and non-structural proteins. Antibodies (polyclonal and monoclonal) made to any of these antigens can be used to detect the antigen as well as to isolate the antigens and to remove virus, proteins, or nucleic acids from a sample, e.g., a blood sample. Antibodies to HP-4 antigens can be used in diagnostic assays to detect viral infection. Any suitable sample, including blood, saliva, sputum, etc., can be used in a diagnostic assay of the invention. Such antibodies can also be used in therapeutic applications to inhibit or prevent viral infection.

The HP-4 antigens of the invention can also be used in diagnostic application to detect anti-HP-4 antigen antibodies in infected or exposed subjects. HP-4 antigens of the invention can also be used therapeutically, as vaccines for acute or latent infections, e.g., whole virus vaccines, protein or subunit vaccines, nucleic acid vaccines (encoding viral proteins, ORFs or genomes for intracellular expression and secretion or cell surface display; can be targeted to specific cell types using promoters and vectors), and dendritic cell vaccines. This dendritic cell approach can be used to form a virus-specific vaccine, by first producing a specific class of dendritic cells using cell culture (often autologous cells from the patient), and then loading these cells with antigen that is specific to a patient's tumor. Once administered to patients, these dendritic cell vaccines are intended to work by triggering a T-cell immune system response against the patient's virally infected cells.

HP-4 nucleic acids can be used to produce infectious clones, e.g., for production of recombinant viral particles, including empty capsids or capsids containing a recombinant (e.g., wild type or further comprising a heterologous nucleic acid) or modified (e.g., mutated) HP-4 genome, which may be replication competent or incompetent, using the methods disclosed in U.S. Pat. Nos. 6,558,676; 6,132,732; 6,001,371; 5,916,563; 5,827,647; 5,508,186; 6,379,885; 6,287,815; 6,204,044; and 5,449,608. Such particles are useful as gene transfer vehicles, and as vaccines, and for use in diagnostic applications and for drug discovery assays for antiviral compounds, as discussed below.

Finally, the HP-4 virus, nucleic acids and proteins of the invention can be used to assay for antiviral compounds, including compounds that inhibit (1) viral interactions at the cell surface, e.g., viral transduction (e.g., block viral cell receptor binding or internalization); (2) viral replication and gene expression, e.g., viral replication (e.g., by inhibiting non-structural protein activity, origin activity, or primer binding), viral transcription (promoter or splicing inhibition, non-structural protein inhibition), viral protein translation, protein processing (e.g., cleavage or phosphorylation); and (3) viral assembly and egress, e.g., viral packaging, and virus release.

DEFINITIONS

Parvovirus HP-4 refers to both the genetic components of the virus, e.g., the genome (positive or negative) and RNA transcripts thereof (either sense or antisense), proteins encoded by the genome (including structural and nonstructural proteins), and viral particles. The term "parvovirus HP-4" or a nucleic acid encoding "parvovirus HP-4" refer to nucleic acids and polypeptide polymorphic variants, alleles, mutants, and interspecies homologs that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 150, 200, 250, 300, 350, 400, 450, 500, 550, 600, 650, 700, 750, 800, 850, 900, 950, 1000, or more nucleic acids, up to the full length sequence, to the nucleotide sequence of SEQ ID NO:1; (2) bind to antibodies, e.g., polyclonal or monoclonal antibodies, raised against an immunogen comprising an amino acid sequence of a protein encoded by an open reading frame of SEQ ID NO:2 or 3, and conservatively modified variants thereof, (3) specifically hybridize under stringent hybridization conditions to an anti-sense strand corresponding to a nucleic acid sequence of SEQ ID NO:1, and conservatively modified variants thereof; (4) encoding a protein having an amino acid sequence encoded by a polynucleotide having at least about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 300, 400, 500, 600, 700, 800, 900, 1000, or more amino acids, to a protein encoded by an open reading frame of SEQ ID NO:2 or 3.

The invention contemplates isolated polynucleotide having at least about 10, 12, 15, 20, 25, 30, 35, 40, 45, 50, 55, 60, 65, 70, 75, 80, 85, 90, 95, 100, 120, 130, 140, 150, 160, 170, 180, 190, 200, 225, 250, 300, 325, 350, 400, 450, 500, 550, 600, 650, 700, or 750 contiguous nucleotides of: (1) a nucleotide sequence of SEQ ID NO:1, (2) a nucleotide sequence that encodes the amino acid sequence encoded by SEQ ID NO:2; or (3) a nucleotide sequence that encodes the amino acid sequence encoded by SEQ ID NO:3. The invention further contemplates polynucleotides, as well as polypeptides encoded by such polynucleotides, where the polynucleotides have greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity over a region of at least about 25, 50, 100, 150, 200, 250, 300, 350, 400, 450, 500, 550, 600, 650, 700, 750, 800, 850, 900, 950, 1000, 1500, 1991, 2000, 2384, 2500 or more contiguous nucleotides, up to the full length sequence, of: (1) a nucleotide sequence of SEQ ID NO:1, (2) a nucleotide sequence of SEQ ID NO:2 or a nucleotide sequence that encodes the amino acid sequence encoded by SEQ ID NO:2; or (3) a nucleotide sequence of SEQ ID NO:3 or a nucleotide sequence that encodes the amino acid sequence encoded by SEQ ID NO:3. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules.

HP-4 parvovirus nucleic acids, including, e.g., a genome or an RNA transcript, include any nucleic acid that has at least about 12, 15, 16, 18, 20, 22, 24, 25, or up to about 50 contiguous nucleotides that hybridize to SEQ ID NO:1 or other polynucleotide sequence encoding an HP-4 nucleic acid or polypeptide, e.g., a polypeptide encoded by SEQ ID NO:2 or 3. In preferred embodiments, the hybridization is performed under stringent conditions.

"Protein encoded by parvovirus HP-4" or "protein encoded by parvovirus HP-4 open reading frame (ORF)" refers to structural and non-structural parvoviral proteins encoded by nucleic acids that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleic acids, up to the full length sequence, to the nucleotide sequence of SEQ ID NO:2 (corresponding to the first underlined portion of SEQ ID NO:1 in FIG. 7, starting with an ATG and ending with a TAA, e.g., nucleotides 283-2274) or SEQ ID NO:3 (corresponding to the second underlined portion of SEQ ID NO:1 in FIG. 7, starting with an ATG and ending with a TAA, e.g., nucleotides 2378-5122); (2) bind to antibodies, e.g., polyclonal or monoclonal antibodies, raised against an immunogen comprising an amino acid sequence of a protein encoded by an open reading frame of SEQ ID NO:2 (corresponding to the first underlined portion of SEQ ID NO:1 in FIG. 7, starting with an ATG and ending with a TAA, e.g., nucleotides 283-2274) or SEQ ID NO:3 (corresponding to the second underlined portion of SEQ ID NO:1 in FIG. 7, starting with an ATG and ending with a TAA, e.g., nucleotides 2378-5122), and conservatively modified variants thereof, (3) specifically hybridize under stringent hybridization conditions to an anti-sense strand corresponding to a nucleic acid sequence of SEQ ID NO:2 (corresponding to the first underlined portion of SEQ ID NO:1 in FIG. 7, starting with an ATG and ending with a TAA, e.g., nucleotides 283-2274) or SEQ ID NO:3 (corresponding to the second underlined portion of SEQ ID NO:1 in FIG. 7, starting with an ATG and ending with a TAA, e.g., nucleotides 2378-5122), and conservatively modified variants thereof, (4) encoding a protein having an amino acid sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more amino acids, to a protein encoded by an open reading frame of SEQ ID NO:2 (corresponding to the first underlined portion of SEQ ID NO:1 in FIG. 7, starting with an ATG and ending with a TAA, e.g., nucleotides 283-2274) or SEQ ID NO:3 (corresponding to the second underlined portion of SEQ ID NO:1 in FIG. 7, starting with an ATG and ending with a TAA, e.g., nucleotides 2378-5122). The amino acid sequence of the structural and non-structural viral proteins encoded by HP-4 ORF #1 (SEQ ID NO:2) and #2 (SEQ ID NO:3) can be easily identified by one of skill in the art, using the algorithms disclosed herein, by aligning the HP-4 sequence with other parvovirus sequences, including B19.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence or amino acid sequence of FIGS. 1-3), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a parvovirus HP-4, polymorphic variants, alleles, orthologs, and conservatively modified variants, or splice variants, or portions thereof, can be selected to obtain only those polyclonal antibodies that are specifically immunoreactive with parvovirus HP-4 and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The phrase "functional effects" in the context of assays for testing compounds that modulate activity of a parvovirus HP-4 includes the determination of a parameter that is indirectly or directly under the influence of a parvovirus HP-4, e.g., a phenotypic or chemical effect, such as the ability to increase or decrease viral genome replication, viral RNA and protein production, virus packaging, viral particle production (particularly replication competent viral particle production), cell receptor binding, viral transduction, cellular infection, antibody binding, inducing a cellular or humoral immune response, viral protein enzymatic activity, etc. "Functional effects" include in vitro, in vivo, and ex vivo activities. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for a protein; measuring inducible markers or transcriptional activation of a protein; measuring binding activity or binding assays, e.g. binding to antibodies; measuring changes in ligand or substrate binding activity; measuring viral replication; measuring cell surface marker expression; measurement of changes in protein levels; measurement of RNA stability; identification of downstream or reporter gene expression (CAT, luciferase, 13-gal, GFP and the like), e.g., via chemiluminescence, fluorescence, calorimetric reactions, antibody binding, and inducible markers.

"Inhibitors", "activators", and "modulators" of parvovirus HP-4 nucleic acid and polypeptide sequences are used to refer to activating, inhibitory, or modulating molecules identified using in vitro and in vivo assays of the parvovirus nucleic acid and polypeptide sequences. Inhibitors are compounds that, e.g., bind to, partially or totally block activity, decrease, prevent, delay activation, inactivate, desensitize, or down regulate the activity or expression of parvovirus HP-4, e.g., antagonists. "Activators" are compounds that increase, open, activate, facilitate, enhance activation, sensitize, agonize, or up regulate parvovirus HP-4 activity, e.g., agonists. Inhibitors, activators, or modulators also include genetically modified versions of parvovirus HP-4, e.g., versions with altered activity, as well as naturally occurring and synthetic ligands, substrates, antagonists, agonists, antibodies, peptides, cyclic peptides, nucleic acids, antisense molecules, ribozymes, small chemical molecules and the like. Such assays for inhibitors and activators include, e.g., expressing parvovirus HP-4 in vitro, in cells, or cell membranes, applying putative modulator compounds, and then determining the functional effects on activity, as described above.

Samples or assays comprising parvovirus HP-4 that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of parvovirus HP-4 is achieved when the activity value relative to the control is about 80%, preferably 50%, more preferably 25-0%. Activation of parvovirus HP-4 is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

An "siRNA" molecule or an "RNAi molecule refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also PCT/US03/07237, herein incorporated by reference in its entirety.

An siRNA molecule or RNAi molecule is "specific" for a target nucleic acid if it reduces expression of the nucleic acid by at least about 10% when the siRNA or RNAi is expressed in a cell that expresses the target nucleic acid.

Isolation of Parvovirus HP-4 Genome and Genes

This invention relies on routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)). Parvovirus HP-4, polymorphic variants, orthologs, and alleles that are substantially identical to an amino acid sequence encoded by nucleic acids of SEQ ID NO:1 can be isolated using nucleic acid probes and oligonucleotides under stringent hybridization conditions, by screening DNA libraries or by using PCR. Genes encoding parvoviral proteins can be isolated using cDNA libraries. Alternatively, expression libraries can be used to clone the parvovirus HP-4, polymorphic variants, orthologs, and alleles by detecting expressed homologs immunologically with antisera or purified antibodies made against human parvovirus HP-4 or portions thereof.

To make a cDNA library to clone parvovirus genes expressed by the genome, one should choose a source that is rich in the RNA of choice. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and optionally mechanically sheared or enzymatically digested. The fragments are then separated by gradient centrifugation from undesired sizes and are constructed in suitable vectors. These vectors are packaged in vitro. Recombinant vectors can be analyzed, e.g., by plaque hybridization as described in Benton & Davis, *Science* 196:180-182 (1977). Colony hybridization is carried out as generally described in Grunstein et al., *Proc. Natl. Acad. Sci. USA*, 72:3961-3965 (1975).

A preferred method of isolating parvovirus HP-4 and orthologs, alleles, mutants, polymorphic variants, splice variants, and conservatively modified variants combines the use of synthetic oligonucleotide primers and amplification of an RNA or DNA template (see Example 1, below, see also U.S. Pat. Nos. 4,683,195 and 4,683,202; *PCR Protocols: A Guide to Methods and Applications* (Innis et al., eds, 1990)). Methods such as polymerase chain reaction (PCR and RT-PCR) and ligase chain reaction (LCR) can be used to amplify nucleic acid sequences directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of parvovirus HP-4 encoding mRNA in physiological samples, for nucleic acid sequencing, or for other purposes. Genes amplified by the PCR reaction can be purified from agarose gels and cloned into an appropriate vector.

Gene expression of parvovirus HP-4 can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids encoding a parvovirus HP-4 genome or protein can be used with high density oligonucleotide array technology (e.g., GeneChip™) to identify parvovirus HP-4, orthologs, alleles, conservatively modified variants, and polymorphic variants in this invention. In the case where the homologs being identified are linked to modulation of the cell cycle, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat.*

Biotechnol. 14:1675-1680 (1996); Gingeras et al., *Genome Res.* 8:435-448 (1998); Hacia et al., *Nucleic Acids Res.* 26:3865-3866 (1998).

The gene of choice is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene or genome, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing parvovirus HP-4 proteins and nucleic acids.

After the expression vector is introduced into the cells, the transfected cells are cultured under conditions favoring expression of the protein of choice, which is recovered from the culture using standard techniques identified below.

Purification of Polypeptides

Either naturally occurring or recombinant parvovirus HP-4 proteins encoded by ORF #1 or ORF #2 can be purified for use in diagnostic assays, for making antibodies (for diagnosis and therapy) and vaccines, and for assaying for anti-viral compounds. As described above, SEQ ID NOS: 2 and 3 encode structural proteins. (Naturally occurring proteins can be purified, e.g., from human tissue samples. Recombinant protein can be purified from any suitable expression system.

The protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein could be purified using immunoaffinity columns. Recombinant protein can be purified from any suitable source, include yeast, insect, bacterial, and mammalian cells.

A. Purification of Recombinant Protein

Methods for production and purification of recombinant protein from a bacterial or eukaryotic (e.g., yeast, mammalian cell, and the like) system are well known in the art. Recombinant proteins are expressed by transformed host cells, (e.g., bacteria) in large amounts, typically after promoter induction; but expression can be constitutive. Promoter induction with IPTG is one example of an inducible promoter system. Host cells are grown according to standard procedures in the art. Where the host cell is a bacterial cell, fresh or frozen bacteria cells are used for isolation of protein.

Recombinant proteins, particularly when expressed in bacterial host cells, may form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, where the host cell is a bacterium, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein can also be separated from other proteins on the basis of its size, net surface charge, hydrophobicity, and affinity for ligands or substrates. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Immunological Detection of Polypeptides and Nucleic Acids

In addition to the detection of a parvovirus HP-4 gene and gene expression using nucleic acid hybridization technology, one can also use immunoassays to detect parvovirus HP-4 proteins, virus, and nucleic acids of the invention. Such assays are useful for, e.g., therapeutic and diagnostic applications. Immunoassays can be used to qualitatively or quantitatively analyze protein, virus, and nucleic acids. A general overview of the applicable technology can be found in Harlow & Lane, *Antibodies: A Laboratory Manual* (1988).

A. Production of Antibodies

Methods of producing polyclonal and monoclonal antibodies that react specifically with parvovirus HP-4 protein, virus and nucleic acids are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of a parvovirus HP-4 protein, virus or nucleic acid may be used to produce antibodies specifically reactive with the parvovirus HP-4. For example, a recombinant parvovirus HP-4 protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-parvovirus HP-4 proteins and nucleic acids, using a competitive binding immunoassay. Specific polyclonal antisera and monoclonal antibodies will usually bind with a $K_d$ of at least about 0.1 mM, more usually at least about 1 µM, preferably at least about 0.1 M or better, and most preferably, 0.01 µM or better. Antibodies specific only for a particular parvovirus HP-4 protein can also be made by subtracting out other cross-reacting proteins, e.g., from other human parvoviruses or other non-human parvoviruses. In this manner, antibodies that bind only to the protein of choice may be obtained.

Once the specific antibodies against a parvovirus HP-4 protein, virus or nucleic acid in are available, the antigen can be detected by a variety of immunoassay methods. In addition, the antibody can be used therapeutically. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

Protein, in this case HP-4 protein which is either associated with or separate from an HP-4 viral particle, can be detected and/or quantified using any of a number of well recognized immunological binding assays (see, e.g., U.S. Pat. Nos. 4,366,241; 4,376,110; 4,517,288; and 4,837,168). HP-4 viral particles may be detected based on an epitope defined by the viral proteins as presented in a viral particle and/or an epitope defined by a viral protein that is separate from a viral particle (e.g., such as may be present in an infected cell). As used in this context, then, "antigen" is meant to refer to an HP-4 polypeptide as well as HP-4 viral particles. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice. The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled parvovirus HP-4 protein nucleic acid or a labeled anti-parvovirus HP-4 antibody. Alternatively, the labeling agent may be a third moiety, such a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111: 1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 110° C. to 40° C.

Non-Competitive Assay Formats

Immunoassays for detecting parvovirus HP-4 protein, virus and nucleic acid in samples may be either competitive or noncompetitive, and may be either quantitative or non-quantitative. Noncompetitive immunoassays are assays in which antigen is directly detected and, in some instances the amount of antigen directly measured. In a "sandwich" assay, for example, the anti-parvovirus HP-4 antibodies can be bound directly to a solid substrate on which they are immobilized. These immobilized antibodies then capture the parvovirus HP-4 antigen present in the test sample. Proteins thus immobilized are then bound by a labeling agent, such as a second anti-parvovirus HP-4 antigen antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays parvovirus HP-4 antigen present in a sample is detected indirectly by detecting a decrease in a detectable signal associated with a known, added (exogenous) parvovirus HP-4 antigen displaced (competed away) from an anti-parvovirus HP-4 antigen antibody by the unknown parvovirus HP-4 antigen present in a sample. In this manner, such assays can also be adapted to provide for an indirect measurement of the amount of HP-4 antigen present in the sample. In one competitive assay, a known amount of parvovirus HP-4 antigen is added to a sample and the sample is then contacted with an antibody that specifically binds to the parvovirus HP-4 antigen. The amount of exogenous parvovirus HP-4 antigen bound to the antibody is inversely proportional to the concentration of parvovirus HP-4 antigen present in the sample. In a particularly preferred embodiment, the antibody is immobilized on a solid substrate. The amount of parvovirus HP-4 antigen bound to the antibody may be determined either by measuring the amount of parvovirus HP-4 antigen present in parvovirus HP-4 antigen/antibody complex, or alternatively by measuring the amount of remaining uncomplexed protein. The amount of parvovirus HP-4 antigen may be detected by providing a labeled parvovirus HP-4 antigen.

A hapten inhibition assay is another competitive assay. In this assay the known parvovirus HP-4 antigen is immobilized on a solid substrate. A known amount of anti-parvovirus HP-4 antigen antibody is added to the sample, and the sample is then contacted with the immobilized parvovirus HP-4 antigen. The amount of anti-parvovirus HP-4 antigen bound to the known immobilized parvovirus HP-4 antigen is inversely proportional to the amount of parvovirus HP-4 antigen present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a parvovirus HP-4 antigen can be immobilized to a solid support. Proteins are added to the assay that compete for binding of the antisera to the immobilized antigen. The ability of the added proteins to compete for binding of the antisera to the immobilized protein is compared to the ability of the parvovirus HP-4 antigen to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a parvovirus HP-4 antigen, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the parvovirus HP-4 antigen that is required to inhibit 50% of binding, then the second protein is said to specifically bind to the polyclonal antibodies generated to parvovirus HP-4 antigen.

Other Assay Formats

Western blot (immunoblot) analysis is used to detect and quantify the presence of parvovirus HP-4 antigen in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the parvovirus HP-4 antigen. The anti-parvovirus HP-4 antigen antibodies specifically bind to the parvovirus HP-4 antigen on the solid support. These antibodies may be directly labeled or alternatively may be subsequently detected using labeled antibodies (e.g., labeled sheep anti-mouse antibodies) that specifically bind to the anti-parvovirus HP-4 antigen antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize parvovirus HP-4 antigen, or secondary antibodies that recognize anti-parvovirus HP-4 antigen.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidatases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Diagnostic Assays and Kits for HP-4 Proteins and Nucleic Acids

The present invention provides diagnostic assays to detect HP-4 parvovirus, HP-4 parvovirus nucleic acids (genome and genes), HP-4 antibodies in an infected subject, and HP-4 proteins. In one embodiment, HP-4 nucleic acid is detected using a nucleic acid amplification-based assay, such as a PCR assay, e.g., in a quantitative assay to determine viral load. In another embodiment, HP-4 antigens are detected using a serological assay with antibodies (either monoclonal or polyclonal) to antigens encoded by ORF#1 or ORF #2. HP-4 antibodies in a sample can be detected using HP-4 antigens encoded by ORF#1 or #2. These methods can also be used for removing the parvovirus from a blood sample. Donated blood contaminated with parvovirus HP-4 can be dangerous for immunocompromised recipients or other susceptible individuals such as pregnant women.

A. Assays for HP-4 Proteins and Antibodies to HP-4 Antigens

In one embodiment of the present invention, the presence of parvovirus, parvovirus nucleic acid, or parvovirus protein in a sample is determined by an immunoassay. Enzyme mediated immunoassays such as immunofluorescence assays (IFA), enzyme linked immunosorbent assays (ELISA) and immunoblotting (western) assays can be readily adapted to accomplish the detection of the parvovirus or parvoviral proteins. An ELISA method effective for the detection of the virus can, for example, be as follows: (1) bind an anti-paroviral antibody or antigen to a substrate; (2) contact the bound receptor with a fluid or tissue sample containing the virus, a viral antigen, or antibodies to the virus; (3) contact the above with an antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect presence of an antiparvoviral antibody in the sample or a specific parvoviral protein as well as the virus.

Another immunologic technique that can be useful in the detection of parvoviruses is the competitive inhibition assay, utilizing monoclonal antibodies (MABs) specifically reactive with the virus. Briefly, serum or other body fluids from the subject is reacted with an antibody bound to a substrate (e.g. an ELISA 96-well plate). Excess serum is thoroughly washed away. A labeled (enzyme-linked, fluorescent, radioactive, etc.) monoclonal antibody is then reacted with the previously reacted parvovirus virus-antibody complex. The amount of inhibition of monoclonal antibody binding is measured relative to a control. MABs can also be used for detection directly in samples by IFA for MABs specifically reactive for the antibody-virus complex.

Alternatively, a parvovirus antigen and/or a patient's antibodies to the virus can be detected utilizing a capture assay. Briefly, to detect antibodies to parvovirus in a patient sample, antibodies to the patient's immunoglobulin, e.g., anti-IgG (or IgM) are bound to a solid phase substrate and used to capture the patient's immunoglobulin from serum. A parvovirus, or reactive fragments of a parvovirus, are then contacted with the solid phase followed by addition of a labeled antibody. The amount of patient parvovirus specific antibody can then be quantitated by the amount of labeled antibody binding.

Additionally, a micro-agglutination test can also be used to detect the presence of parvovirus in test samples. Briefly, latex beads are coated with an antibody and mixed with a test sample, such that parvovirus in the tissue or body fluids that are specifically reactive with the antibody crosslink with the receptor, causing agglutination. The agglutinated antibody-virus complexes form a precipitate, visible with the naked eye or by spectrophotometer. Other assays include serologic assays, in which the relative concentrations of IgG and IgM are measured.

In the diagnostic methods described above, the sample can be taken directly from the patient or in a partially purified form. The antibody specific for a particular parvovirus (the primary reaction) reacts by binding to the virus. Thereafter, a secondary reaction with an antibody bound to, or labeled with, a detectable moiety can be added to enhance the detection of the primary reaction. Generally, in the secondary reaction, an antibody or other ligand which is reactive, either specifically or nonspecifically with a different binding site (epitope) of the virus will be selected for its ability to react with multiple sites on the complex of antibody and virus. Thus, for example, several molecules of the antibody in the secondary reaction can react with each complex formed by the primary reaction, making the primary reaction more detectable.

The detectable moiety can allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, (1988)).

B. Assays for HP-4 Nucleic Acids

As described herein, a HP-4 infection may also, or alternatively, be detected based on the level of an HP-4 RNA or DNA in a biological sample. Primers from HP-4 can be used for detection of HP-4, diagnosis, and determination of HP-4 viral load. Any suitable primer can be used to detect the genome, nucleic acid sub sequence, ORF, or protein of choice, using, e.g., methods described in US 20030104009. For example, the subject nucleic acid compositions can be used as single- or double-stranded probes or primers for the detection of HP-4 mRNA or cDNA generated from such mRNA, as obtained may be present in a biological sample (e.g., extracts of human cells). The HP-4 polynucleotides of the invention can also be used to generate additional copies of the polynucleotides, to generate antisense oligonucleotides, and as triple-strand forming oligonucleotides. For example, two oligonucleotide primers may be employed in a polymerase chain reaction (PCR) based assay to amplify a portion of HP-4 cDNA derived from a biological sample, wherein at least one of the oligonucleotide primers is specific for (i.e., hybridizes to) the HP-4 polynucleotide. The amplified cDNA is then separated and detected using techniques well known in the art, such as gel electrophoresis. Similarly, oligonucleotide probes that specifically hybridize to a HP-4 polynucleotide may be used in a hybridization assay to detect the presence of the HP-4 polynucleotide in a biological sample. These and other uses are described in more detail below.

Nucleic acid probes specific to HP-4 can be generated using the polynucleotide sequences disclosed herein. The probes are preferably at least about 12, 15, 16, 18, 20, 22, 24, or 25 nt fragments of a contiguous sequence of SEQ ID NO: 1 or other polynucleotide sequence encoding an HP-4 nucleic acid or polypeptide. Nucleic acid probes can be less than about 200 bp, 150 bp, 100 bp, 75 bp, 50 bp, 60 bp, 40 bp, 30 bp, 25 bp 2 kb, 1.5 kb, 1 kb, 0.5 kb, 0.25 kb, 0.1 kb, or 0.05 kb in length. The probes can be produced by, for example, chemical synthesis, PCR amplification, generation from longer polynucleotides using restriction enzymes, or other methods well known in the art.

The polynucleotides of the invention, particularly where used as a probe in a diagnostic assay, can be detectably labeled. Exemplary detectable labels include, but are not limited to, radiolabels, fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrho-damine (TAMRA)), radioactive labels, (e.g. $^{32}P$, $^{35}S$, and $^{3}H$), and the like. The detectable label can involve two stage systems (e.g., biotin-avidin, hapten-anti-hapten antibody, and the like).

The invention also includes solid substrates, such as arrays, comprising any of the polynucleotides described herein. The polynucleotides are immobilized on the arrays using methods known in the art. An array may have one or more different polynucleotides.

Any suitable qualitative or quantitative methods known in the art for detecting specific HP-4 nucleic acid (e.g., RNA or DNA) can be used. HP-4 nucleic acid can be detected by, for example, in situ hybridization in tissue sections, using methods that detect single base pair differences between hybridizing nucleic acid (e.g., using the Invader™ technology described in, for example, U.S. Pat. No. 5,846,717), by reverse transcriptase-PCR, or in Northern blots containing poly A+mRNA, and other methods well known in the art. For detection of HP-4 polynucleotides in blood or blood-derived samples, the use of methods that allow for detection of single base pair mismatches is preferred.

Using the HP-4 nucleic acid as a basis, nucleic acid probes (e.g., including oligomers of at least about 8 nucleotides or more) can be prepared, either by excision from recombinant polynucleotides or synthetically, which probes hybridize with the HP-4 nucleic acid, and thus are useful in detection of HP-4 virus in a sample, and identification of infected individuals, as well as further characterization of the viral genome(s). The probes for HP-4 polynucleotides (natural or derived) are of a length or have a sequence which allows the detection of unique viral sequences by hybridization. While about 6-8 nucleotides may be useful, longer sequences may be preferred, e.g., sequences of about 10-12 nucleotides, or about 20 nucleotides or more. Preferably, these sequences will derive from regions which lack heterogeneity among HP-4 viral isolates.

Nucleic acid probes can be prepared using routine methods, including automated oligonucleotide synthetic methods. A complement to any unique portion of the HP-4 genome will be satisfactory, e.g., a portion of the HP-4 genome that allows for distinguishing HP-4 from other viruses that may be present in the sample, e.g., other parvovirus such as B19. For use as probes, complete complementarity is desirable, though it may be unnecessary as the length of the fragment is increased.

For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled with a detectable label. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the HP-4 genome or portion thereof (e.g., to all or a portion of a sequence encoding an HP-4 GAG polypeptide). Therefore, usually high stringency conditions are desirable in order to prevent or at least minimize false positives. However, conditions of high stringency should only be used if the probes are complementary to regions of the viral genome which lack heterogeneity among HP-4 viral isolates. The stringency of hybridization is determined by a number of factors during hybridization and during the washing procedure, including temperature, ionic strength, length of time, and concentration of formamide. These factors are outlined in, for example, Sambrook et al. (1989), "Molecular Cloning; A Laboratory Manual", Second Edition (Cold Spring Harbor Press, Cold Spring Harbor, N.Y.).

Generally, it is expected that the HP-4 sequences will be present in a biological sample (e.g., blood, cells, and the liked) obtained from an infected individual at relatively low levels, e.g., at approximately $10^2$-$10^4$ HP-4 sequences per $10^6$ cells. This level may require that amplification techniques be used in hybridization assays. Such techniques are known in the art.

For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT Publication No. WO84/03520 and European application no. EPA124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPA 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands.

Non-PCR-based, sequence specific DNA amplification techniques can also be used in the invention to detect HP-4 sequences. An example of such techniques include, but are not necessarily limited to the Invader assay, see, e.g., Kwiatkowski et al. *Mol Diagn*. December 1999; 4(4):353-64. See also U.S. Pat. No. 5,846,717.

A particularly desirable technique may first involve amplification of the target HP-4 sequences in sera approximately 10,000 fold, e.g., to approximately 10 sequences/mL. This may be accomplished, for example, by the polymerase chain reactions (PCR) technique described which is by Saiki et al. (1986), by Mullis, U.S. Pat. No. 4,683,195, and by Mullis et al. U.S. Pat. No. 4,683,202. Other amplification methods are well known in the art. In a preferred embodiment, a sample suspected of comprising the parvoviral nucleic acid is contacted with at least one primer that hybridizes to a nucleotide sequence of SEQ ID NO:1, said contacting being under conditions suitable for amplification of an amplification product from a parvoviral nucleic acid in the sample.

The probes, or alternatively nucleic acid from the samples, may be provided in solution for such assays, or may be affixed to a support (e.g., solid or semi-solid support). Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads.

In one embodiment, the probe (or sample nucleic acid) is provided on an array for detection. Arrays can be created by, for example, spotting polynucleotide probes onto a substrate (e.g., glass, nitrocellulose, and the like) in a two-dimensional matrix or array. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734. Arrays are particularly useful where, for example a single sample is to be analyzed for the presence of two or more nucleic acid target regions, as the probes for each of the target regions, as well as controls (both positive and negative) can be provided on a single array. Arrays thus facilitate rapid and convenient analysis.

C. Kits

The invention further provides diagnostic reagents and kits comprising one or more such reagents for use in a variety of diagnostic assays, including for example, immunoassays such as ELISA and "sandwich"-type immunoassays, as well as nucleic acid assay, e.g., PCR assays. In a related embodiment, the assay is performed in a flow-through or strip test format, wherein the binding agent is immobilized on a membrane, such as nitrocellulose. Such kits may preferably include at least a first peptide, or a first antibody or antigen binding fragment of the invention, a functional fragment thereof, or a cocktail thereof, or a first oligo pair, and means for signal generation. The kit's components may be pre-attached to a solid support, or may be applied to the surface of a solid support when the kit is used. The signal generating means may come pre-associated with an antibody or nucleic acid of the invention or may require combination with one or more components, e.g., buffers, nucleic acids, antibody-enzyme conjugates, enzyme substrates, or the like, prior to use.

Kits may also include additional reagents, e.g., blocking reagents for reducing nonspecific binding to the solid phase surface, washing reagents, enzyme substrates, enzymes, and the like. The solid phase surface may be in the form of microtiter plates, microspheres, or other materials suitable for immobilizing nucleic acids, proteins, peptides, or polypeptides. An enzyme that catalyzes the formation of a chemiluminescent or chromogenic product or the reduction of a chemiluminescent or chromogenic substrate is one such component of the signal generating means. Such enzymes are well known in the art. Where a radiolabel, chromogenic, fluorigenic, or other type of detectable label or detecting means is included within the kit, the labeling agent may be provided either in the same container as the diagnostic or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

Assays for Modulators of Parvovirus HP-4

A. Assays

Modulation of a parvovirus HP-4, and corresponding modulation of the cell cycle, e.g., tumor cell, proliferation, can be assessed using a variety of in vitro and in vivo assays, including cell-based models. Such assays can be used to test for inhibitors and activators of parvovirus HP-4. Modulators of parvovirus HP-4 are tested using either recombinant or naturally occurring protein of choice, preferably human parvovirus HP-4.

Preferably, the parvovirus HP-4 will have the sequence as encoded by a sequence as shown in SEQ ID NO:1 or a conservatively modified variant thereof. Alternatively, the parvovirus HP-4 of the assay will be derived from a eukaryote and include an amino acid subsequence having substantial amino acid sequence identity to a sequence as shown in SEQ ID NO:1. Generally, the amino acid sequence identity will be at least 60%, preferably at least 65%, 70%, 75%, 80%, 85%, or 90%, most preferably at least 95%.

Measurement of modulation of a parvovirus HP-4 or a cell expressing parvovirus HP-4, either recombinant or naturally occurring, can be performed using a variety of assays, in vitro, in vivo, and ex vivo, as described herein. A suitable physical, chemical or phenotypic change that affects activity, e.g., enzymatic activity, cell surface marker expression, viral replication and proliferation can be used to assess the influence of a test compound on the polypeptide of this invention. When the functional effects are determined using intact cells or animals, one can also measure a variety of effects.

In Vitro Assays

Assays to identify compounds with parvovirus HP-4 modulating activity can be performed in vitro. Such assays can used full length parvovirus HP-4 or a variant thereof, or a mutant thereof, or a fragment thereof, such as a RING domain. Purified recombinant or naturally occurring protein can be used in the in vitro methods of the invention. In addition to purified parvovirus HP-4, the recombinant or naturally occurring protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, etc. A wide variety of assays can be used to identify parvovirus HP-4-modulator binding, including labeled protein-protein binding assays, electrophoretic mobility shifts, immunoassays, enzymatic assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the protein is washed, interference with binding, either of the potential modulator or of the known ligand or substrate, is determined. Often, either the potential modulator or the known ligand or substrate is labeled.

Cell-Based In Vivo Assays

In another embodiment, the parvovirus HP-4 is expressed in a cell, and functional, e.g., physical and chemical or phenotypic, changes are assayed to identify modulators of the cell cycle. Any suitable functional effect can be measured, as described herein. The parvovirus HP-4 can be naturally occurring or recombinant. Also, fragments of the parvovirus HP-4 or chimeric proteins can be used in cell based assays. In addition, point mutants in essential residues required by the catalytic site can be used in these assays.

B. Modulators

The compounds tested as modulators of parvovirus HP-4 can be any small organic molecule, or a biological entity, such as a protein, e.g., an antibody or peptide, a sugar, a nucleic acid, e.g., an antisense oligonucleotide or a ribozyme or RNAi, or a lipid. Alternatively, modulators can be genetically altered versions of a parvovirus HP-4. Typically, test compounds will be small organic molecules, peptides, circular peptides, RNAi, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a parvovirus HP-4, or a cell or tissue expressing an parvovirus HP-4, either naturally occurring or recombinant. In another embodiment, the invention provides solid phase based in vitro assays in a high throughput format, where the parvovirus HP-4 is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for parvovirus HP-4 in vitro, or for cell-based or membrane-based assays comprising a parvovirus HP-4. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:4). Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Vaccines

Within certain aspects, HP-4 virus, proteins or peptides and immunogenic fragments thereof, and/or polynucleotides, as well as anti-HP-4 antibodies and/or T cells, may be incorporated into pharmaceutical compositions or immunogenic compositions (e.g., vaccines). Whole virus vaccine (live and attenuated, or replication incompetent, or killed) or subunit vaccines, such as structural or non-structural HP-4 proteins or immunogenic fragments thereof, encoded by SEQ ID NO:2 or 3, can be used to treat or prevent HP-4 infections by eliciting an immune response in a subject. Alternatively, a pharmaceutical composition may comprise an antigen-presenting cell (e.g., a dendritic cell) transfected with a HP-4 polynucleotide such that the antigen-presenting cell expresses an HP-4 peptide.

Pharmaceutical compositions comprise one or more such vaccine compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see, e.g., U.S. Pat. No. 4,235,877). Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Vaccine preparation is generally described in, for example, Powell and Newman, eds., *Vaccine Design* (the subunit and adjuvant approach), Plenum Press (NY, 1995). Vaccines may be designed to generate antibody immunity and/or cellular immunity such as that arising from CTL or CD4+ T cells.

Pharmaceutical compositions and vaccines within the scope of the present invention may also contain other compounds, which may be biologically active or inactive. For example, one or more immunogenic portions of other antigens may be present, either incorporated into a fusion polypeptide or as a separate compound, within the composition or vaccine. Polypeptides may, but need not, be conjugated to other macromolecules as described, for example, within U.S. Pat. Nos. 4,372,945 and 4,474,757. Pharmaceutical compositions and vaccines may generally be used for prophylactic and therapeutic purposes.

Nucleic acid vaccines encoding a genome, structural protein or non-structural protein or a fragment thereof of HP-4 can also be used to elicit an immune response to treat or prevent HP-4 infection. Numerous gene delivery techniques are well known in the art, such as those described by Rolland (1998) *Crit. Rev. Therap. Drug Carrier Systems* 15:143-198, and references cited therein. Appropriate nucleic acid expression systems contain the necessary DNA sequences for expression in the patient (such as a suitable promoter and terminating signal). In a preferred embodiment, the DNA may be introduced using a viral expression system (e.g., vaccinia, pox virus, retrovirus, or adenovirus), which may involve the use of a non-pathogenic (defective), replication competent virus. Suitable systems are disclosed, for example, in Fisher-Hoch et al. (1989) *Proc. Natl. Acad. Sci. USA* 86:317-321; Flexner et al. (1989) *Ann. N.Y. Acad. Sci.* 569: 86-103; Flexner et al. (1990) *Vaccine* 8:17-21; U.S. Pat. Nos. 4,603,112, 4,769,330, 4,777,127 and 5,017,487; WO 89/01973; GB 2,200,651; EP 0,345,242; WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993) *Proc. Natl. Acad. Sci. USA* 90:11498-11502; Guzman et al (1993) *Circulation* 88:2838-2848; and Guzman et al. (1993) *Cir. Res.* 73:1202-1207. Techniques for incorporating DNA into such expression systems are well known to those of ordinary skill in the art. The DNA may also be "naked," as described, for example, in Ulmer et al. (1993) *Science* 259:1745-1749 and reviewed by Cohen (1993) *Science* 259:1691-1692. The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences,* $17^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Identification of Three New Human Viruses

Materials and Methods

Study Subjects

Specimens for analysis were selected from stored plasma obtained from subjects screened for acute HIV infection in the UCSF Options Project but found to be HIV negative. The screening process has been described previously (Hecht et al., *Aids* 16, 1119-29 (2002)). In brief, participants with recent possible exposure to HIV and with two or more symptoms compatible with acute retroviral syndrome were screened for anti-HIV antibodies and plasma HIV-1 RNA (bDNA, Bayer Diagnostics, Emeryville, Calif.). Study staff performed a structured interview in which participants were asked whether they had any of 21 symptoms compatible with acute HIV infection or other viral illnesses, including fever, rash, fatigue, malaise, phyrangitis, nausea, diarrhea, headache, myalgias, and arthralgias. All subjects consented to participate in a protocol approved by the UCSF Institutional Review Board before having specimens collected.

DNAse Sequence Independent Single Primer Amplification (DNAse-SISPA)

One hundred microliters of each plasma sample was diluted with $H_2O$ to a final volume of 300 µL and filtered through a 0.22 µm filter (Ultrafree MC, Millipore, Bedford, Mass.). Filtered plasma was treated with 250 U DNase I (Roche Diagnostics, Mannheim, Germany) for 2 hours at 37° C. to remove contaminating human DNA. DNase I resistant nucleic acids were purified using either the QIAamp Viral RNA Mini Kit or the QIAamp DNA Blood Mini Kit (Qiagen, Valencia, Calif.). To detect viral RNA first-strand cDNA synthesis was performed in an 80 µL reaction containing 25 mM Tris-HCl (pH 8.3,) 37.5 mM KCl, 15 mM $MgCl_2$, 0.01 M DTT, 5 mM dNTP, 40 U RNase inhibitor, 5 pmol random hexamers (GIBCO, Gaithersburg, Md.), and 200 U of Superscript 11 RNase H⁻RT (Invitrogen, Carlsbad, Calif.) at 42° C. for 1 hour. Thirteen µL of second-strand cDNA synthesis mix containing 50 mM 2-Mercaptoethanol, 500 µg/mL BSA, IU of RNaseH and 4 U of DNA Polymerase I (Invitrogen, Carlsbad, Calif.) was added to the first-strand reaction mix and incubated at 12° C. for 1 hour followed by 1 hour at 22° C. Following second-strand synthesis samples were heated at 72° C. for 15 minutes. To detect viral DNA a complementary strand was generated by incubating 30 of the 60 ul of extracted DNA, 5 units of Klenow fragment (exo-) (New England Biolabs, Beverly, Mass.) and 5 pmol of random hexamers in 1× EcoPol buffer and at 37° C. for 1 hour. Samples were then digested with the restriction enzyme Csp6.I (Fermentas, Hanover, Md.) for 1 hour at 37° C. and restricted DNA was purred using a QIAquick column (Qiagen, Valencia, Calif.) and eluted in eluted into 50 µL of 10 mM TrisHCl. Adaptors composed of hybridized oligonucleotides NBam24 5' AGGCAACTGTGCTATCCGAGGGAG 3' (SEQ ID NO:5) and NCsp11 5' TACTCCCTCGG 3' (SEQ ID NO:6) (80 pmoles) were then ligated to the restricted DNA in a 20 µL reaction containing 10 units of T4 DNA ligase (Invitrogen, Carlsbad, Calif.) at room temperature for 5 minutes (Allander et al., T., *Proc Natl Acad Sci USA* 98, 11609-14 (2001)). Two µL of the ligation reaction was then added to a 48 µL PCR reaction containing 20 mM Tris-HCl (pH 9), 50 mM KCl, 2.5 mM MgCl₂, 2 mM dNTP, 50 pmol of NBam24, and 2.5 units of Taq Polymerase (Promega, Madison, Wis.). Cycling conditions were as follows; 94° C. 1 min, 72° C. 3 min, for 40 cycles.

Analysis of DNAse-SISPA Amplified DNA

Amplified PCR products were analyzed by PAGE. Distinct DNA bands were excised, pooled and crushed using a 1.5 mL pellet pestle in 750 µL of 10 mM Tris-HCl (pH 8.5), and incubated overnight a at room temperature. DNA from excised bands was purified using QIAquick columns (Qiagen) and eluted into 50 µL of 10 mM Tris-HCl (pH 7.0). Purified DNA (10 µL) was ligated into pGEM-T-Easy as per the manufacturer's instructions (Promega, Madison Wis.) and 2 µL ligation mix was transformed into *E. coli* TOP-10 cells (Invitrogen, Carlsbad, Calif.). Positive clones were selected and plasmid DNA purified. Subcloned inserts were sequenced using flanking vector primers and the BigDye 3.0 Dye Terminator Cycle Sequencing Kit (Applied Biosystems, Foster City, USA) on an AB13700 Sequencer.

Amplification of Full Viral Genomes

Subcloned and sequenced fragments of HP-4 (located at the extreme 5' and 3' positions) were used to design PCR primers (pr-3B-04303-46F: 5'TGCCTTACCATTCACTGACGC3' (SEQ ID NO:7) and pr-7R-04303-174R: 5'TTGGCAAGGGTAAAAGGCAT3' (SEQ ID NO:8)) to amplify the intervening 4.3 kb region. The fragment was then sequenced using primer walking. The 5' end of the HP-4 genome was amplified and sequenced using the 5' RACE kit (Invitrogen, Carlsbad, Calif.). The HP-4 genome was first linearly amplified (60 cycles; 94° C. for 30 s, 50° C. for 30 s, 72° C. for 2 min) using Taq polymerase and HP-4 specific primer pr4303-377R 5'ACTCCTTCTGCAGCTGGTGTC3' (SEQ ID NO:9). Amplification products were purified using QIAquick columns (Qiagen) and a poly-C tail added to the 3' end using deoxycytidine and Terminal deoxynucleotidyl transferase (Invitrogen, Carlsbad, Calif.). The 5' region was then amplified with 2.5 units of Taq polymerase using an anchor abridged primer (5' 5'GGCCACGCGTCGACTAGTACGGGIIGGGIIGGGTTG3' (SEQ ID NO:10)) (Invitrogen, Carlsbad, Calif.), pr4303-377R and Taq polymerise (2.5 U) for 60 cycles of 94° C. for 30 s, 50° C. for 30 s and 72° C. for 2 min.

Complete circular genomes for both SAV-1 and SAV-2 were generated by PCR using abutting primers of opposite polarity designed within a subcloned region. Primers used for amplification of SAV-1 were prSAV-1-IF-784F, 5'GTGGCGAATGGCTGAGTTTACCY (SEQ ID NO:11) and prSAV-1-IR-988R, 5'GTGTTGGTGTCTGTAAAAGGTCATAACAC3' (SEQ ID NO:12) and for SAV-2 were pr5412-2201, 5'GTNNNGAATGGCTGAGTTTACY (SEQ ID NO:13) and pr5412-97, 5'TCTTCTTACCTTGTACCGGCG3' (SEQ ID NO:14). Amplification reactions contained 2.5 U Taq polymerase and cycling conditions included 40 cycles of 94° C. for 18 sec, 54° 0 for 21 sec and 72° C. for 1 minute 30 sec. The fragments were then sequenced using primer walking.

Phylogenetic Analysis of Parvovirus HP-4

Phylogenetic analysis was performed using sequences representing full-length genomes from all species from the Parvovirinae subfamily (Lukashov and Goudsmit, *J Virol* 75, 2729-40 (2001)). In addition, sequences of recently identified parvoviruses, including two bovine parvoviruses (BPV-2, AF406966, and BPV-3, AF406967) (Allander et al., T., *Proc Natl Acad Sci USA* 98, 11609-14 (2001)), a A6 human virus (AY064476) (Nguyen et al., *Virology* 301, 374-80 (2002)) and the minute virus of canines (MVC, AF495-467) (Schwartz et al., *Virology* 302, 219-23 (2002)) were included. Sequences were aligned using Clustal X (Thompson et al., *Nucleic Acids Res* 22, 4673-80 (1994)), and a neighbor-joining tree (nucleotide distance with Jukes-Cantor correction, pair-wise gap deletion), with bootstrap resampling (100 replicates) was constructed using the MEGA software (Kumar et al., *Comput Appl Biosci* 10, 189-91 (1994)).

Phylogenetic Analysis of TTV-Like Viruses

TTV-like sequences amplified from two of the study subjects were aligned to a dataset comprised of previously described complete genome sequences of TTV genotypes (AB008394 [TA278; genotype 1]; AF122916 [JA1, genotype 2]; AF247138 [T3PB, genotype 3]; AB017613 [TUS01, genotype 11]; AB028668 [TJN01, genotype 12] and AB028669 [TJN02, genotype 13]) and human TTV-like minivirus (TLMV) sequences (AB041962 [TGP96]; AB038628 [CLC205]; AB038626 [CLC138]; AB026931 [CBD279]; AB026930 [CBD231]; AB038629 [NLC023]; AB038630 [NLC026]; AB038631 [NLC030]; AB026929 [CBD203]; AB038627 [CLC156] and AF291073 [PB4TL]). The dataset also included complete genome sequences from non-human primates (sequence accession numbers are indicated in parenthesis); chimpanzee; PtTTV6 (AB041957) and Pt-TTV8-II (ABO41963), macaque (*Maccaca fasicularis*); Mf-TTV3 (AB041958) and Mf-TTV9 (AB041959), tamarin (*Sanguinis oedipus*); So-TTV2 (AB041960); owl monkey (*Aotus trivirgatus*); At-TTV3 (AB041961) and tree shrew (*Tupaia belangeri chinensis*); Tbc-TTV14 (AB057358) and other mammals; canine, Cf-TTV 10 (AB076002), porcine, Sd-TTV31 (AB076001) and feline, Fc-TTV4 (AB076003) (Okamoto. et al., *Virology* 277, 368-78 (2000); Inami et al., *J Gen Virol* 82, 2041-50 (2001); Okamoto et al., *J Gen Virol* 83, 1291-7 (2002)).

Non-coding regions of the genomes were aligned using CLUSTALW with default settings and edited by eye to maximize alignment of regions of homology. The large ORF was aligned using the inferred amino acid sequence of the encoded protein in CLUSTALW. The introduction of increasing gap penalties identified several regions of sequence homology in the coding sequence. Phylogenetic comparison of sequences was carried out using maximum likelihood (HKY85 model with gamma distribution for estimation of likelihoods), maximum parsimony and neighbor joining methods (Jukes-Cantor and Timura-Nei distances) using both PAUP and MEGA software packages (Kumar et al., *Bioinformatics* 17, 1244-5 (2001)).

Results

Detection of HCV Sequences in Seropositive Samples

Figure 1B:
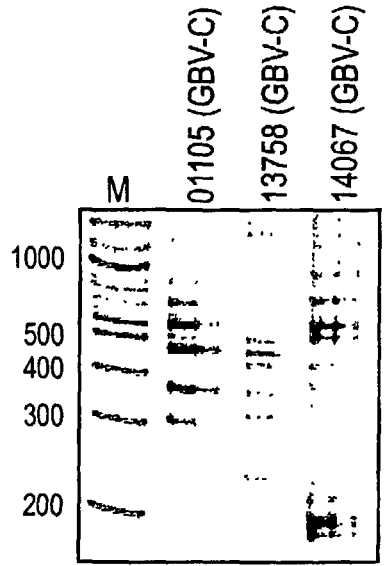
Figure 2A:
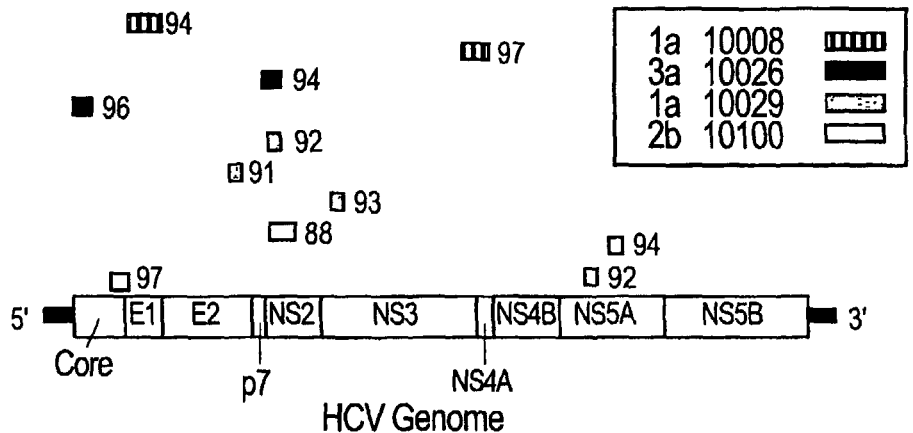
FIG. 2A-C. Genomic location of subcloned viral sequences homologous to A: HCV, B: GBV-C/HCV and C: HBV. Patient ID numbers are indicated and viral subtypes are indicated for HCV sequences. Nucleotide similarity values (%) are indicated adjacent to the subcloned fragments.

The efficiency of DNase-SISPA was initially tested using six HCV seropositive plasmas. Following DNAse-SISPA and PAGE distinct band patterns were observed by PAGE for 5 of the 6 samples (FIG. 1A). One sample showed only a DNA smear. Following the subcloning and sequencing of gel-purified bands HCV sequences were identified using; BLASTn similarity searches (FIG. 2A). Four of five HCV positive samples for which distinct bands were observed yielded multiple sequence fragments belonging to HCV genotypes 1a, 2b and 3a.

Selection of Patients with Viral Infection Syndrome

From 261 individuals presenting with acute viral syndrome, who were screened for HIV1 infection between June 1996 and June 2002, the 25 subjects with the most potential virus infection related symptoms and available cryopreserved plasma specimens were selected for this study. These 25 subjects had a range of 11-17 of the 21 potential virus infection related symptoms assessed at screening. The most common reported symptoms (in order) were fatigue, malaise, night sweats, and headache. Twenty-three of the 25 subjects were male, and all reported potential sexual exposure to HIV in the prior 6 months; 2 also reported using injection drugs in the prior 6 months.

Detection of DNA and RNA viruses

Figure 2B:
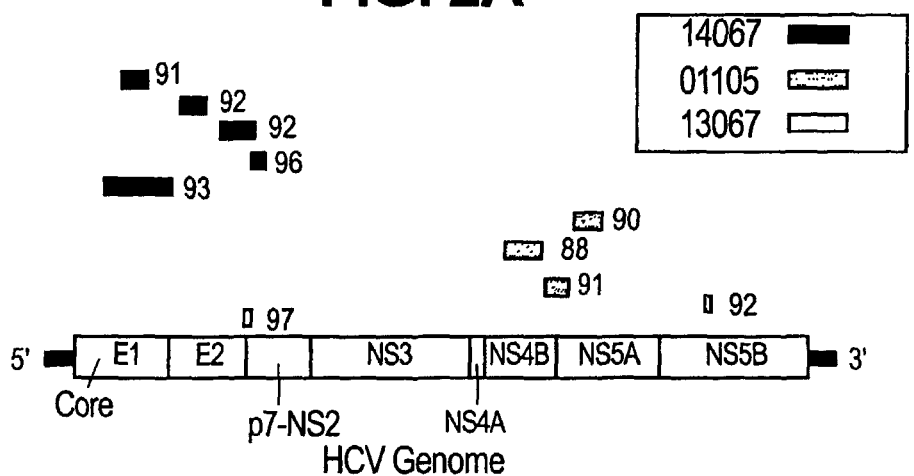
Figure 2C:
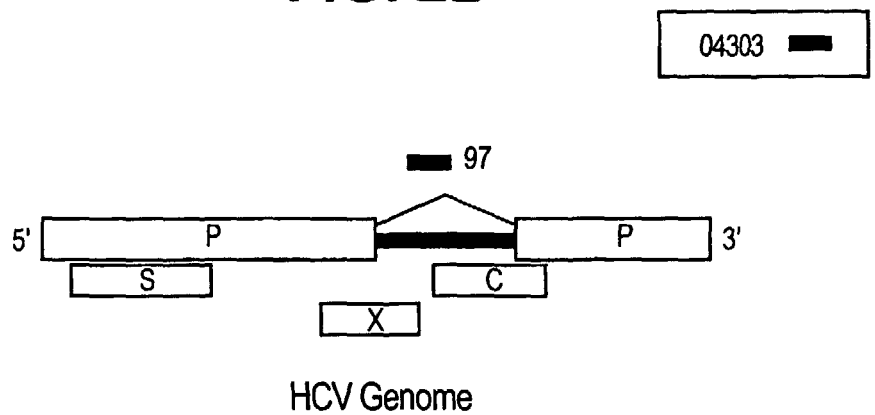

All samples were processed by DNase-SISPA for the presence of both RNA and DNA viruses (see materials and methods). Samples from three individuals processed for RNA viruses yielded distinct bands (FIG. 1B) that upon subcloning and sequencing followed by BLASTn analyses were shown to be highly homologous to the flavivirus GBV-C/HGV with E scores of 0 to $10^{-28}$) (FIG. 2B).

Figure 1C:
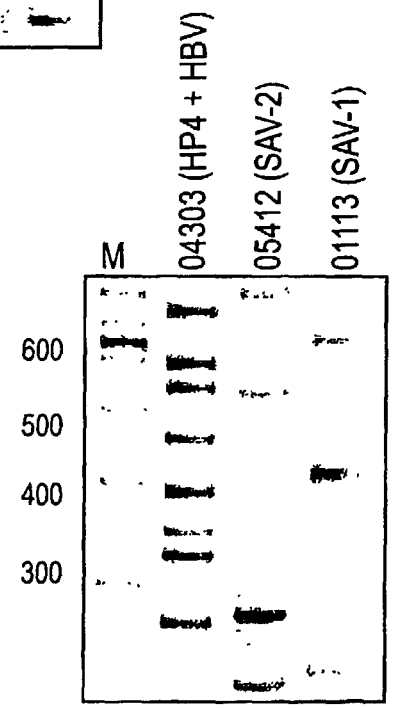

An additional 3 samples screened for DNA viruses also yielded distinct PCR bands (FIG. 1C). A subcloned sequence from subject 04303 was highly homologous to HBV (BLASTn E score of 10-39), (FIG. 2C) while all other sequences resulted in very weak BLASTn E scores>0.002.

In order to search for similarity at the amino acid level DNA sequences generated were then analyzed using tBLASTx. tBLASTx translates a sequence into its six possible reading frames and searches for amino acid similarity against the entire sequence database translated in the same fashion. Sample 04303 derived sequences produced tBLASTx E scores of 10-11 to 10-44 against animal parvoviruses. Translated sequences from the other two samples (05412 and 01113) also showed similarity (E scores of 10-4 to 10-23) to the anelloviruses TorqueTenoVirus (TTV) and TorqueTenoMiniVirus (TTMV) (Hino, S., *Rev Med Virol* 12, 151-8 (2002)). To further characterize these viral sequences complete genomes were PCR amplified and sequenced.

Cloning of New Human Parvovirus

Two methods were used to amplify the full genome of the virus with homology to parvoviruses. Firstly, PCR primers were designed based on DNAse-SISPA generated fragment sequences expected by tBLASTx to be located near the 5' and 3' ends of a parvovirus genome. Long range PCR yielded the intervening portions of the parvovirus genome. The extreme 5' end of the linear genome was then acquired using the 5' RACE method. The resulting, virtually full-length genome sequence was 5268 by in length and contained 2 open reading frames (ORF) (FIG. 3). tBLASTx searches showed that ORF1 and ORF2 encoded proteins showed significant homology to the non-structural and capsid proteins of other parvoviruses, respectively. Based on its genome size, ORF structure, homology to parvoviruses and its human host this linear DNA virus was tentatively named human parvovirus 4 (HP-4). The infected patient was a daily injection drug user who was homeless at the time of evaluation. He complained of fatigue, night sweats, phyrangitis, neck stiffness, vomiting, diarrhea, arthralgias, and confusion.

Phylogenetic Analysis of New Parvovirus HP-4

Figure 4:
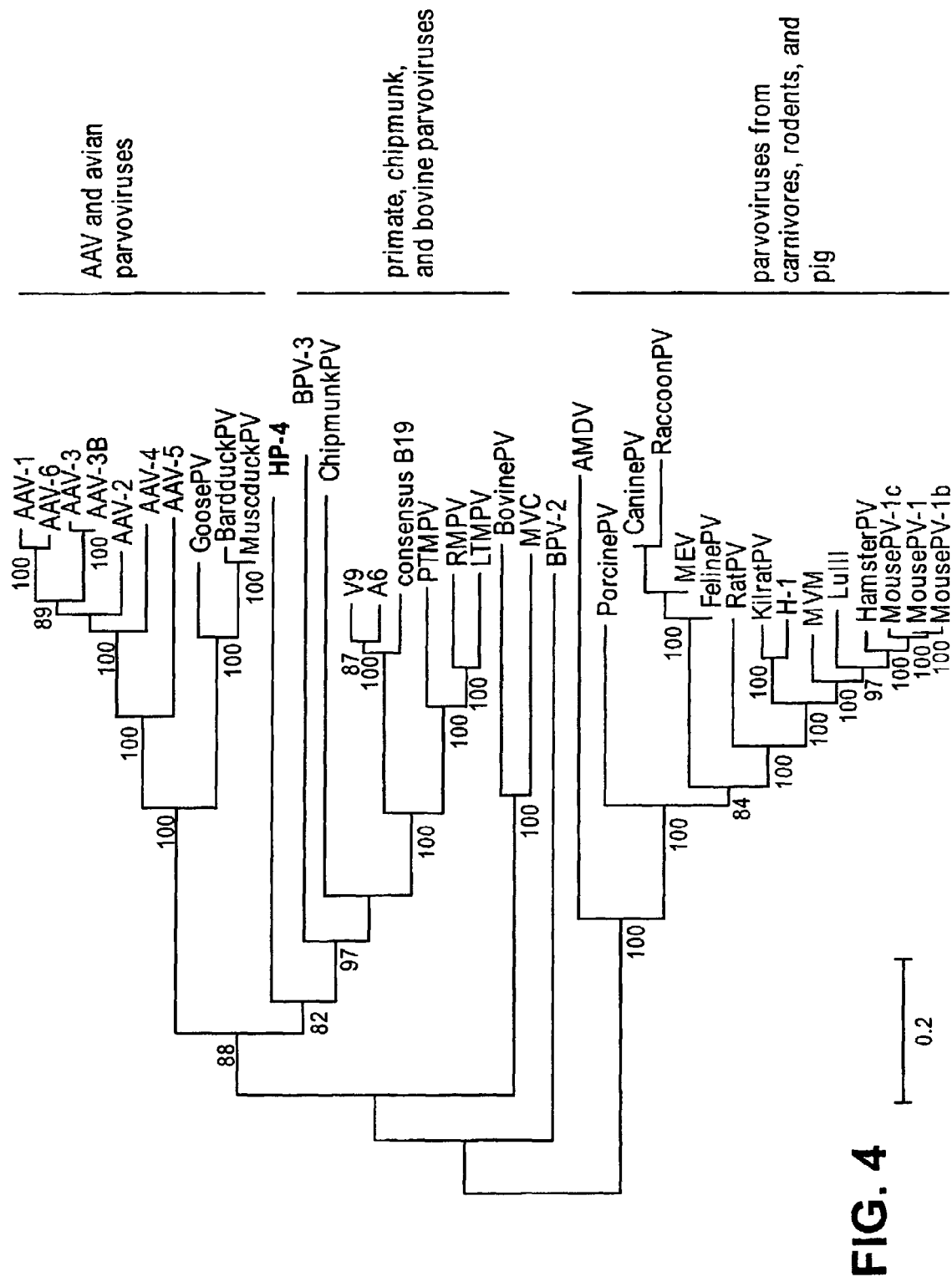
FIG. 4. Phylogenetic analysis of the HP-4 genome and other members of the Parvoviridae subfamily.

Three major evolutionary groups of viruses have recently been identified within the Parvovirinae subfamily (Lukashov and Goudsmit, *J Virol* 75, 2729-40 (2001)). To establish the evolutionary relationship of HP-4 to other parvoviruses phylogenetic analysis of full-length genomes from all known members of the Parvovirinae subfamily was performed (FIG. 4).

Our analysis indicated that HP-4 was not closely related to any known parvoviruses and represent a deeply-rooted lineage between two parvovirus groups containing; (i) adeno-associated viruses (AAV) and avian parvoviruses and (ii) primate, chipmunk and bovine parvovirus 3 (FIG. 4). Phylogenetic analyses were also performed separately for ORF 1 and ORF2. The topologies of these trees were similar to that of the full-genome tree (data not shown). Recombination analysis using the bootscan method was performed on HP-4 to determine if it was a recombinant of other known parvoviruses. Short genetic regions within the HP-4 genome that were more similar to the chipmunk parvovirus and bovine parvoviruses 3 were identified. However, the short length of these regions of homology and the low bootstrap support for these associations suggested that HP-4 was not a recombinant (data not shown). Our results therefore indicated that HP-4 is a unique member of the Parvoviridae family that is not closely related to any other known human or animal parvovirus.

Cloning of New Anelloviruses SAV-1 and SAV-2

Figure 5A:
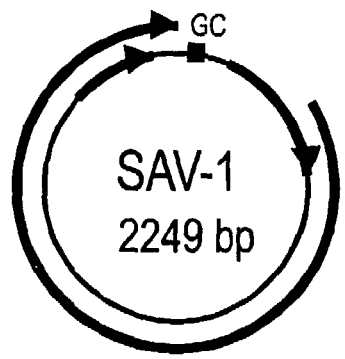
FIG. 5A-F. The genetic organization of (A) SAV-1, (B) SAV-2, (C) TTMV, (D) TTMV-238, (E) TTV, and (F) TTV-JT41F. Arrows represent open reading frames detected in each virus. The GC rich region (GC) has a GC content greater than 72%. ORFinder (NCBI) was used to determine the open reading frames for each virus as described in materials and methods.
Figure 5B:
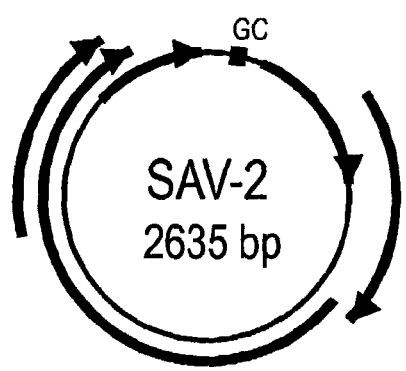
Figure 5C:
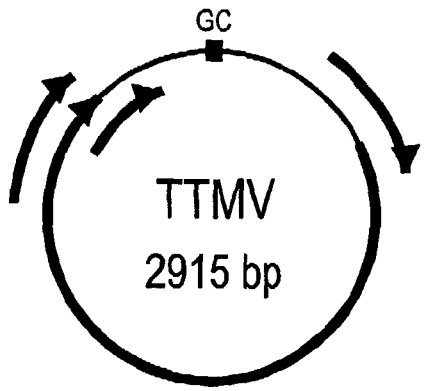
Figure 5D:
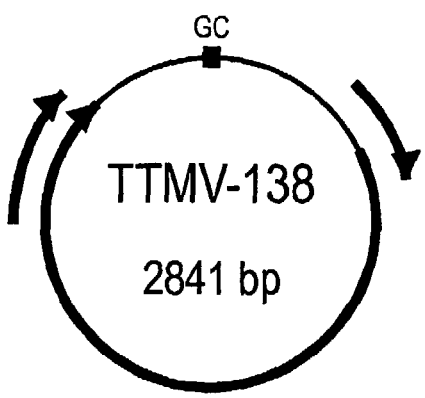
Figure 5E:
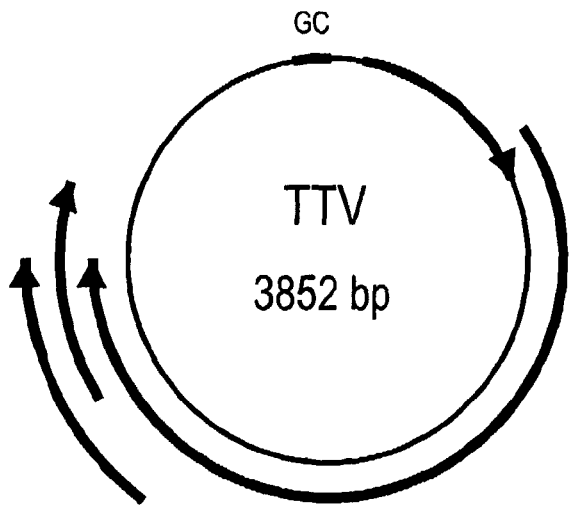
Figure 5F:
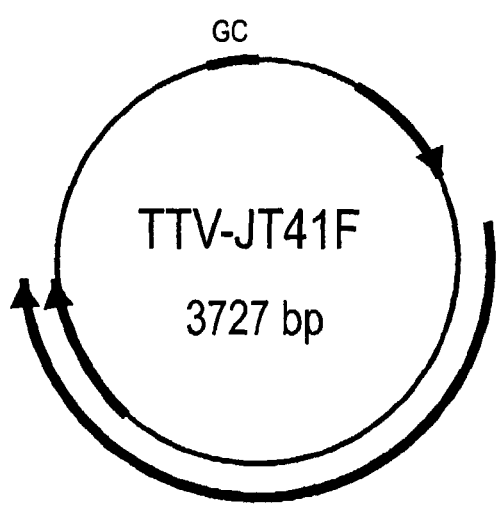

To acquire the remainder of the anellovirus-like genomes sequence gaps were also filled by PCR and sequenced using primer walking. Anelloviruses have circular genomes (Hino, S., *Rev Med Virol* 12, 151-8 (2002)) and their sequences were therefore assembled using long range PCR with amplification primers facing in opposite directions. The viral sequence from patient 01113 was 2249 by in length and contained 3 ORF (FIG. 5A) and the virus from sample 05412 was 2635 by in length and contained 5 potential ORF (FIG. 5B). Such an orf structure differed from those observed for TTV and TTMV which have 3 to 4 ORF and larger genomes (FIG. 5C-D) (Hino, S., *Rev Med Virol* 12, 151-8 (2002)). These two viral sequences were classified as anelloviruses based on their circular DNA nature and the presence of regions of homology to TTV and TTMV in the large open reading frame and untranslated region. The provisional names assigned to these viruses from samples 01113 and 05412 are Small Anellovirus 1 (SAV-1) and Small Anellovirus 2 (SAV-2), respectively. The patient infected with SAV1 was an homosexual male with one recent sexual partner and a history of injection drug use. He developed symptoms that lasted 1-2 weeks including fatigue, headaches, fevers, might sweats, nausea, diarrhea, genital ulcers, and a rash. The man infected with SAV2 had multiple male sexual partners prior to developing symptoms and never used injection drugs. He developed symptoms that lasted 1-2 weeks including fatigue, headaches, fevers, night sweats, oral ulcers, diarrhea, 4 kg weight loss, myalgias, and a rash.

Phylogenetic Analysis of New Anelloviruses SAV-1 and SAV-2

Figure 6:
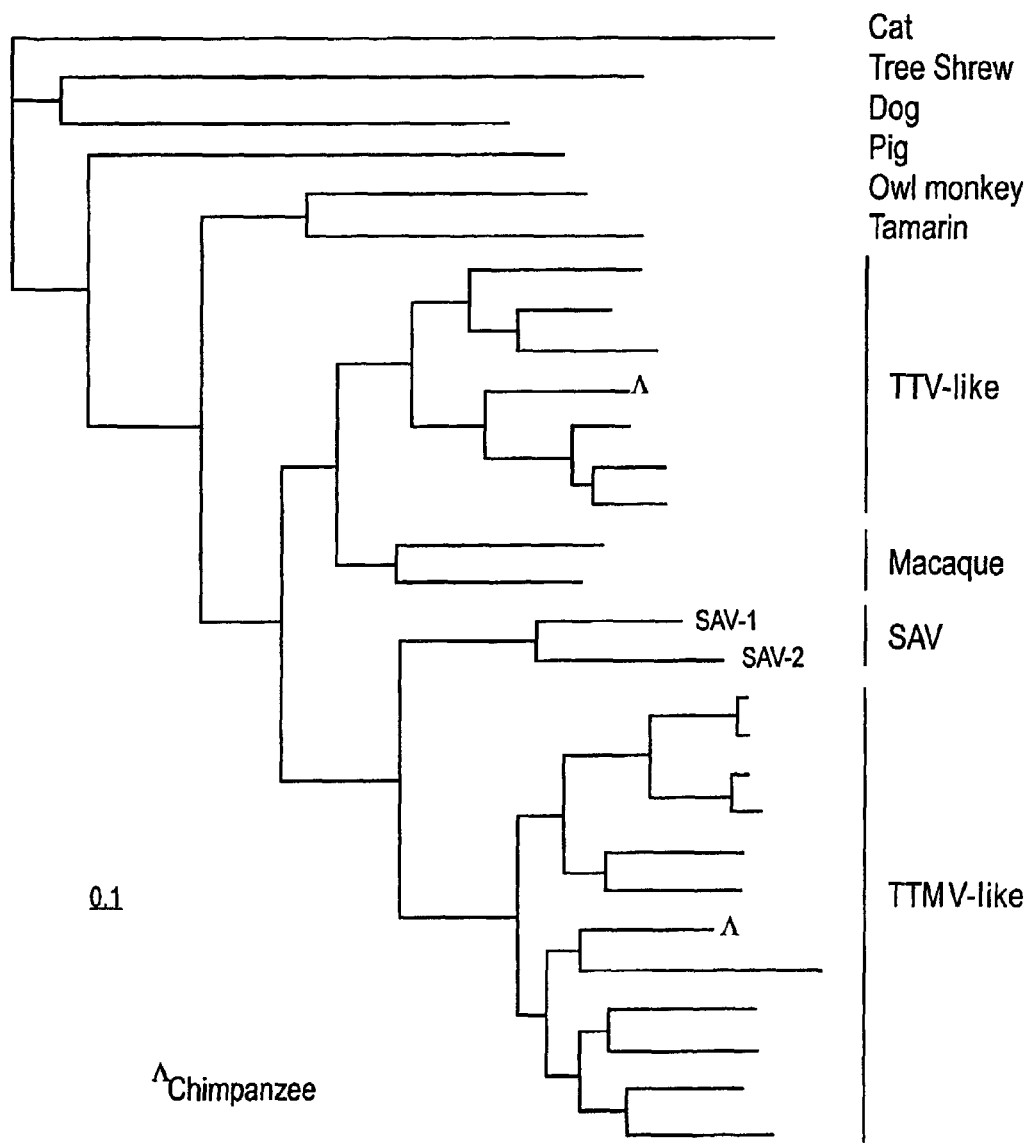
FIG. 6. Phylogenetic analysis of the large ORF of SAV, TTV and TTMV found in a range of mammalian species. All viral sequences originate from human unless otherwise labeled.

To better understand the relationship of SAV-1 and SAV-2 to other anelloviruses, phylogenetic analyses were performed with the long ORF regions (FIG. 6). The high degree of divergence within the anellovirus group and the smaller size of the new genomes prevented the generation of whole genome alignments. This analysis showed that SAV-1 and SAV-2 were related but clustered independently from other known human anellovirus groups (TTV and TTMV-like viruses). SAV sequences were also distinct from TTV-related viruses obtained from chimpanzees and all other non-human primates (FIG. 6). Similar results where obtained with a phylogenetic analysis of the UTR region alone (data not shown). Because of their distinct genomic organization, length and distant phylogenetic relationship to other anelloviruses, we postulate that SAV-1 and SAV-2 may be members of a third group of anelloviruses.

Cloning of Non-Viral Sequences

In addition to the viral sequences described above, we identified sequences with low level similarities (tBLASTx E scores of <2×10$^{-3}$) to bacterial sequences. Detectable similarities to a *Rhodobacter capsulatus* (an anaerobic purple non-sulfur soil bacteria) sequence (E score of 4×10$^{-7}$) and to an uncultured soil bacterial sequence (E score of 10-11) were seen in 2 subclones from patient 04303. A subclone from patient 01113 showed similarities to *Pseudomonas putida* (E score of 10$^{-11}$), and a single subclone from patient 5412 yielded E score of 2.5×10$^{-5}$ to 10$^{-4}$ to *Pseudomonas fluorescens, Neisseria meningitides, Pseudomonas putida* and *Hemophilus influenza*. The wide range of E score to bacterial sequences in the database indicates that these subcloned sequences are not likely to reflect the presence of these exact bacterial species but rather of related species. The majority of subclones derived by DNase-SISPA from these patients showed no detectable similarity to any deposited sequences using either BLASTn or tBLASTx (E score 2×10$^{-3}$).

Discussion

DNase-SISPA was used to analyze 25 plasma samples from individuals presenting with acute viral infection syndromes. GBV-C/HGV was detected in three individuals. A previously un-described parvovirus was detected in another individual who was also coinfected with HBV. Finally, two new anelloviruses were identified in two other individuals. The detection of three previously un-described viruses in such a limited number of individuals reflects the general utility of the DNAse-SISPA method for virus discovery.

GBV-C/HGV RNA or antibodies to its E2 protein have been found in 5.5% of US blood donors and in 89% of intravenous drug users (Dille et al., *J Infect Dis* 175, 458-61 (1997)). GBV-C/HGV viremia has been shown to last at least 3 years (Gutierrez et al., *J Med Virol* 53, 167-73 (1997)). Since the pathogenicity of GBV-C/HGV remains uncertain (Chains et al., *Transfus Clin Biol* 10, 292-306 (2003)), detection of GBV-C/HGV RNA in 3/25 patients may simply reflect its high prevalence rather than a causative role in the symptoms of these individuals.

A recent phylogenetic analysis demonstrated that the Parvovirinae subfamily could be organized into 3 main groups: (a) primate and chipmunk parvoviruses, (b) rodent, pig, and carnivore parvoviruses and (c) adeno-associated viruses and avian parvoviruses (Lukashov and Goudsmit, *J Virol* 75, 2729-40 (2001)). Here we report the finding of a new human parvovirus that clustered independently of these 3 groups of vertebrate parvoviruses (FIG. 4). The detection of a parvovirus highly distinct from the B19 group (B19, V9, and A6 viruses) or AAV group (AAV1 through 6) suggests that the number of parvoviruses able to replicate in humans may be larger than currently appreciated. The PCR primers currently used to test for B19 viremia would not be expected to detect HP-4 (Patou et al., *J Clin Microbiol* 31, 540-6 (1993); Durigon et al., *J Virol Methods* 44, 155-65 (1993)). Transmission of B19 parvovirus occurs via the respiratory route, through blood-derived products transfusion and from mother to fetus (Heegaard et al., *J Clin Microbiol* 40, 933-6 (2002)). HP-4 is therefore also transmitted by similar routes, although it is conceivable that HP-4 is also transmitted from an unidentified animal host to this homeless patient.

Anelloviruses infecting humans include TTV (Mushahwar et al., *Proc Natl Acad Sci USA* 96, 3177-82 (1999)) and its smaller relative TTMV. Both TTV and TTMV are genetically diverse groups and are classified into multiple genotypes (Thom et al., *Virology* 306, 324-33 (2003)). Both viruses are detected at very high frequency in healthy blood donors and primates (Thom et al., *Virology* 306, 324-33 (2003)). The pathogenicity of human anelloviruses remains unknown (Hino, S., *Rev Med Virol* 12, 151-8 (2002); Viazov et al., *J Clin Virol* 11, 183-7 (1998)). Phylogenetic analysis at two loci indicated that SAV-1 and SAV-2 were phylogenetically related but distinct from both the TTV and TTMV groups and may therefore represent two strains of a third group of human anelloviruses. Members of this new anellovirus group may be part of the normal human viral flora with no recognized clinical consequences, not unlike TTV and GBV-C/HGV. Further studies will be required to determine the frequency and potential pathogenic effects of SAV-like viruses in various populations. The discovery of an additional group of TTV-related viruses in humans provides further evidence for the extreme sequence diversity of this viral family.

As in recent non-specific approach to identifying new viral sequences over half the sequences identified were unrelated to any known viral or bacterial species (Breitbart et al., *Proc Natl Acad Sci USA* 99, 14250-5 (2002); Beitbart et al., *J Bacleriol* 185, 6220-3 (2003)) possibly reflecting organisms so divergent from those currently sequenced that even similarity searches at the amino acid level failed to demonstrate any related sequences. The nature of these sequences is being further studied using altered sequence similarity search parameters.

The new TTV-like and parvovirus sequences were also analyzed for their theoretical hybridization potential with a new micro-array using 70 by long oligonucleotides located over the ten most conserved regions of all known viral groups (i.e. the virochip) (Wang et al., *PLoSBiol* 1, E2 (2003); Culley et al., *Nature* 424, 1054-7 (2003)). The two TTV-related viruses were sufficiently related to TTV and TTMV that positive signals would have been expected with some of the TTV specific oligonucleotides while the new HP-4 parvovirus would have remained undetected due to its greater degree of divergence from all pre-existing parvovirus sequences in the database. Because evolutionary relationships remain detectable at the amino acid level for longer time periods of time than they do at the DNA sequence level (Koonin et al., *Sequence—evolution-junction.-computational approaches in comparative Kenomics*, xiii, 461, [11] J of plates (Kluwer Academic, Boston, 2003)) the ability to perform amino acid based similarity searches likely account for the ability to detect more highly divergent viruses using a non-specific PCR/sequencing/translation method than a DNA hybridization based screen.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. An operative promoter and a heterologous nucleic acid molecule comprising SEQ ID NO:2 or 3, or the complement thereof.

2. An operative promoter and a heterologous nucleic acid molecule comprising SEQ ID NO:1, or the complement thereof.

3. An operative promoter and a heterologous nucleic acid molecule comprising a fragment of at least 25 nucleotides of SEQ ID NO:1, or the complement thereof.

4. An operative promoter and a heterologous nucleic acid molecule encoding the polypeptide sequence as set forth in SEQ ID NO:2 or 3.

5. An expression vector comprising the nucleic acid of claim 2 or 4.

6. An isolated host cell comprising the expression vector of claim 5.

* * * * *